(12) United States Patent
Moldavsky et al.

(10) Patent No.: US 6,344,349 B1
(45) Date of Patent: Feb. 5, 2002

(54) PROCESS AND SYSTEM FOR ELECTRICAL EXTRACTION OF INTRACELLULAR MATTER FROM BIOLOGICAL MATTER

(75) Inventors: Leonid Moldavsky, Nazereth-Ilit; Matitiahu Fichman; Kim Shuster, both of Haifa; Mickel Govberg, Haifa, all of (IL)

(73) Assignee: Decant Technologies LLC, Wilmington, DE (US)

( * ) Notice: Subject to any disclaimer, the term of this patent is extended or adjusted under 35 U.S.C. 154(b) by 0 days.

(21) Appl. No.: 09/455,316

(22) Filed: Dec. 6, 1999

(51) Int. Cl.⁷ ............................................. C12N 13/00
(52) U.S. Cl. ................ 435/173.5; 435/173.6; 435/173.7; 435/259; 435/306.1; 422/22; 422/185.15; 422/185.16
(58) Field of Search ............... 435/173.4–173.7, 435/259, 306.1; 422/22, 186, 186.15, 186.16

(56) References Cited

U.S. PATENT DOCUMENTS

| | | | |
|---|---|---|---|
| 4,525,266 A | * | 6/1985 | Groves |
| 5,048,404 A | * | 9/1991 | Bushnell et al. |
| 5,720,921 A | * | 2/1998 | Meserol |
| 5,837,303 A | * | 11/1998 | Hayden |
| 5,989,824 A | * | 11/1999 | Birmingham et al. |

OTHER PUBLICATIONS

Knorr et al., Food applications of high electric field pulses (Mar. 1994) Trends in Food Science and Technology, vol. 5, pp. 71–75.*

Lee et al., A micro cell lysis device (1999) Sensors and Actuators, vol. 73, pp. 74–79.*

Angersbach et al., Electrophysiological model of intact and processed plant tissue: cell disintegration criteria (1999) Biotechnol. Prog., vol. 15, pp. 753–762.*

* cited by examiner

Primary Examiner—Jon P. Weber
Assistant Examiner—Harry J. Guttman
(74) Attorney, Agent, or Firm—Mark M. Friedman

(57) ABSTRACT

A process and system for electrical extraction of intracellular matter from biological matter, and intracellular matter products formed thereby, based on preparing a mixture of biological matter featuring cells, and an electro-conductive liquid, and electrifying the mixture by transmitting controlled cycles of pulses and pauses of electrical current into the mixture by using electrodes, whereby the pulses of electrical current pierce holes into or perforate the cell membranes of the cells, enabling the release of intracellular matter for collecting and separating into target intracellular matter extract and solid waste. Pauses included in each cycle of transmitting pulses of electrical current enable firm control of electrical extraction processing conditions, including extent of extraction, temperature effects, and pressure effects, during the electrical extraction process. Electrical extraction of the present invention is applicable to a wide variety of biological matter originating from human, animal, and plant entities. Intracellular matter extracts so obtained include highly concentrated liquid fertilizer, valuable elements, nutrients, oils, and fats, which are used for manufacturing a diversity of end products of the agricultural, pharmaceutical, cosmetic, and food industries.

12 Claims, 12 Drawing Sheets

PROCESS AND SYSTEM FOR ELECTRICAL EXTRACTION OF INTRACELLULAR MATTER FROM BIOLOGICAL MATTER

FIELD AND BACKGROUND OF THE INVENTION

The present invention relates to a process and system for extraction of cellular matter and, more particularly, to a process and system for electrical extraction of intracellular matter from biological matters such as biological waste materials, and to intracellular matter extracts obtained by implementing the process and system.

Organic matter exists throughout any biological entity, for example, human, animal or plant, living or not. A biological entity is made up of organic and inorganic matter in the forms of cellular and non-cellular matter, where biological cells are known as the building units of a living entity. Cellular matter obtained from waste of biological entities serves as a plentiful source of desirable organic compounds and extracts, such as phenolic compounds, known to be very useful as ingredients in agricultural, pharmaceutical, cosmetic, and food, formulations and products.

Examples of crude biological matter include animal or human compost; plant matter such as raw, dried, extracted or powdered flowers, roots, stems, peels, seeds, fruits and the like; animal solids such as mammal, fish or poultry solid wastes, for example, internal organs or giblets having substantial amounts of fats and oils, derived from growing farms or processing facilities; and liquid organic sewage, such as raw municipal sewage and related sources of liquid organic waste.

There are many processes and steps along the way in obtaining pure organic compounds present in crude biological matter. Upstream processing involves early stages of purification of the above types of biological matter while still in a very crude form. Currently, there are several challenges of upstream processing, among them devising purification methods and systems which are able to separate or isolate intracellular matter, and which are cost effective at the same time in order to be applied to large scale manufacturing environments. There are forms of crude biological matter which simply are not amenable to currently available inexpensive technologies of separation or isolation of cellular matter, as expensive techniques and systems need to be used. Avoiding the use of expensive techniques and systems for obtaining cellular matter from very crude biological matter translates to providing industries, which use purified biological matter as raw materials for manufacturing high performance end products such as medicines, cosmetics, and food and feed flavorings and additives, with low cost raw materials, which ultimately translates to less expensive end products. This effect is desired by both manufacturers and by consumers of the end products.

There is thus a need for, and it would be highly advantageous to have a process and system for separating and obtaining cellular matter from crude biological matter. Extraction is a general type of separation process based on selectively extracting, removing, or drawing out a target substance from a matrix of several substances by chemical, thermal, or mechanical means such as by solvents separation in liquid-liquid extraction, distillation, evaporation, or cold pressing. A plethora of different methods, processes, systems, and apparatus exist for performing extractions.

A commonly used method of liquid-liquid extraction for isolating organic compounds such as phenols, oils, and fats, involves using polar or non-polar organic solvents such as alcohol, isopropanol, acetone, phenol or DMSO as an extracting agent by selectively dissolving target substances. Methods and systems of liquid-liquid extractions have the disadvantages of involving relatively hazardous and costly organic solvents. It would be desirable to eliminate, or at least minimize, quantities of such solvents required for liquid-liquid extraction of organic substances.

Cold pressing is another commonly used method of extracting cellular matter from crude biological matter, which involves subjecting crude biological matter to high pressures, and mechanically pressing out the cellular matter from the crude biological matter. The pressed out cellular matter extract is separated from the remaining crude biological matter matrix, collected, and filtered in order to obtain target substances such as useful organic compounds. Methods of cold pressing usually result in low yields of the target substances, especially in cases where the target substances are not readily pressed out or mechanically separated from crude biological matrices.

There is thus a need for, and it would be useful to have, a process and system for electrical extraction of intracellular matter from biological matter such as biological waste and to obtain intracellular matter extracts by implementing such a process and system, in a cost effective manner.

SUMMARY OF THE INVENTION

The process and system for electrical extraction of intracellular matter of the present invention are based on preparing a mixture of biological matter featuring cells, and an electro-conductive liquid, and electrifying the mixture by transmitting controlled cycles of pulses and pauses of electrical current into the mixture using electrodes, whereby the pulses of electrical current pierce holes into or perforate the membranes of the cells, enabling the release of intracellular matter from the cells for collecting and separating into target intracellular matter extract and solid waste. Including a pause in each cycle of transmitting electrical current enables firm control of processing conditions, including extent of extraction, temperature effects, and pressure effects, during the electrical extraction process.

Electrical extraction of the present invention is applicable to a wide variety of biological matter originating from human, animal, and plant entities. Extracts so obtained include highly concentrated liquid fertilizer, valuable elements and nutrients such as nitrogen, phosphorous, potassium, and their oxides, and, valuable organic compounds such as phenols, oils, and fats, which are used for manufacturing a diversity of end products of the agricultural, pharmaceutical, cosmetic, and food industries.

It is therefore an object of the present invention to provide a process, system, and apparatus for electrical extraction of intracellular matter from biological matter.

It is yet a further object of the present invention to provide an extract of intracellular matter electrically extracted from a biological matter.

It is yet a further object of the present invention to provide a liquid fertilizer extract derived from solid human or animal compost.

It is yet a further object of the present invention to provide a collection of substances derived from intracellular matter of plant material such as flowers, roots, stems, peels, seeds, fruits and the like.

It is yet a further object of the present invention to provide a collection of oils electrically extracted from plant material such as pulp of orange peels, olives, or lavender.

It is yet a further object of the present invention to provide a collection of oils electrically extracted from internal organs or giblets of fish, such as cod liver.

It is yet a further object of the present invention to provide a collection of oils electrically extracted from animal solids, such as -poultry fats sludge flotation.

It is yet a further object of the present invention to provide a process for reducing levels of odor, COD, and BOD in liquid organic sewage, such as raw municipal sewage, by electrical extraction of intracellular matter, where the liquid organic sewage includes biological matter, and the biological matter includes cells.

It is yet a further object of the present invention to provide a system for reducing levels of odor, COD, and BOD in liquid organic sewage by electrical extraction of intracellular matter, where the liquid organic sewage includes biological matter, and the biological matter includes cells.

It is yet a further object of the present invention to provide a liquid organic sewage with reduced levels of odor, COD, and BOD.

Thus, according to the present invention, there is provided a process for electrical extraction of intracellular matter from biological matter, the process comprising the step of electrifying a mixture of the biological matter and an electro-conductive liquid by transmitting at least one series of at least two cycles of electrical current, each of the at least two cycles includes at least one pulse package of the current and at least one pause of the current, into the mixture thereby releasing the intracellular matter from cells of the biological matter.

According to further features in preferred embodiments of the invention described below, each of the at least two cycles of the at least one pulse package and the at least one pause of the electrical current is characterized by at least one of the following parameters: (i) density of the electrical current is in a range of between about $10^2$ to about $10^4$ A/m$^2$; (ii) field strength of the electrical current is in a range of between about $10^2$ to about $10^4$ V/m; (iii) voltage time derivative of the electrical current is in a range of between about $10^6$ to about $10^8$ V/s; (iv) frequency of the electrical current is in a range of between about 10 Hz to about 1 kHz; (v) duration of each pulse package is in a range of between about 1 to about 10 seconds; (vi) duration of each pause is in a range of about 1 second to about 10 seconds; (vii) ratio of the duration of the pulse package to the duration of the pause is in a range of between about 1/1 to about 1/10; (viii) duration of each of the at least two cycles is in a range of between about 2 seconds to about 50 minutes; and (ix) duration of the at least one series of the at least two cycles is in a range of between about 5 seconds to about 60 minutes.

According to still further features in the described preferred embodiments, the electrical current is generated by a power supply unit and is controlled and modulated by a central control unit operating according to phase-pulse regulation, the phase-pulse regulation includes a neutral and at least three phases for regulating the electrical current.

According to still further features in the described preferred embodiments, the pulse package of the electrical current is characterized by polarity selected from the group consisting of unipolar pulses and bipolar pulses, the unipolar pulses being a sequence of the pulses of identical shape and of same sign, the bipolar pulses being a sequence of the pulses of identical shape and of alternating sign, and the shape of the pulses is selected from the group consisting of triangular, rectangular, and sinusoidal.

According to still further features in the described preferred embodiments, the releasing the intracellular matter from the cells of the biological matter takes place during each pulse package of the electrical current and during each pause of the electrical current.

According to still further features in the described preferred embodiments, each of the at least two cycles of the at least one pulse package and the at least one pause of the electrical current is transmitted into the mixture by a mechanism positioned inside each of at least one processor unit, the at least one processor unit is positioned inside a processor assembly, the electrical current is generated by a power supply unit and the transmission of the electrical current is controlled and modulated by a central control unit in electronic communication with the processor assembly.

According to still further features in the description of preferred embodiments, the mechanism for electrifying the biological matter by transmitting into the biological matter the at least one series of the at least two cycles of the at least one pulse package and the at least one pause of the electrical current includes at least two electrodes, each of the at least two electrodes is positioned inside each of the at least one processor unit.

According to still further features in the described preferred embodiments, the mixture enters, is electrified by the electrical current, and exits a processor assembly including at least one processor unit, whereby the processor assembly is configured and operates according to a mode selected from the group consisting of batch and continuous.

According to still further features in the described preferred embodiments, a ratio of the biological matter to the electro-conductive liquid in the mixture is in a range of between about 1/1 to about 1/100 by volume.

According to still further features in the described preferred embodiments, the electro-conductive liquid includes any combination of liquids selected from the group consisting of water, alcohol, and glycerin.

According to still further features in the described preferred embodiments, the process further comprises the steps: (b) supplying the mixture to a processor assembly using a feed supply unit, the processor assembly including at least one processor unit, for exposing the mixture to the electrical current; (c) separating the released intracellular matter from solids using a liquids/solids separator unit, thereby forming a liquid extract including the released intracellular matter; (d) filtering the liquid extract using an extract filtration unit, thereby forming a purer form of the liquid extract; and (e) collecting the purer form of the liquid extract using a liquids collection unit.

According to still farther features in the described preferred embodiments, the liquid extract is filtered through a filter having a filter pore size less than 200 microns.

According to another aspect of the present invention, there is provided a system for electrical extraction of intracellular matter from biological matter, the system comprising: (a) a feed supply unit for mixing the biological matter with an electro-conductive liquid thereby forming a feed supply of a mixture to be fed into at least one processor unit; (b) a processor assembly including the at least one processor unit for receiving the mixture, each of the at least one processor unit includes a mechanism for electrifying the mixture by transmitting into the mixture at least one series of at least two cycles of electrical current, each of the at least two cycles including at least one pulse package of the current and at least one pause of the current, such that the intracellular matter is released from the biological matter of the mixture; (c) a central control unit for controlling and modulating the transmitting of the at least one series of the electrical current into the mixture; (d) a power supply unit controlled by the central control unit for generating and supplying the electrical current to the mechanism; (e) a liquids/solids separator unit for separating the released intracellular matter from solids, thereby forming a liquid extract including the released intracellular matter; (f) an extract filtration unit for filtering the liquid extract, thereby forming a purer form of the liquid extract; and (g) a liquids collection unit for collecting the purer form of the liquid extract.

According to still further features in the described preferred embodiments, each of the at least two cycles of the at least one pulse package and the at least one pause of said electrical current is characterized by at least one of the following parameters: (i) density of the electrical current is in a range of between about $10^2$ to about $10^4$ $A/m^2$; (ii) field strength of the electrical current is in a range of between about $10^2$ to about $10^4$ V/m; (iii) voltage time derivative of the electrical current is in a range of between about $10^6$ to about $10^8$ V/s; (iv) frequency of the electrical current is in a range of between about 10 Hz to about 1 kHz; (v) duration of each pulse package is in a range of between about 1 to about 10 seconds; (vi) duration of each pause is in a range of about 1 second to about 10 seconds; (vii) ratio of the duration of the I10 pulse package to the duration of the pause is in a range of between about 1/1 to about 1110; (viii) duration of each of the at least two cycles is in a range of between about 2 seconds to about 50 minutes; and (ix) duration of the at least one series of the at least two cycles is in a range of between about 5 seconds to about 60 minutes.

According to still further features in the described preferred embodiments, the central control unit operates according to phase-pulse regulation, the phase-pulse regulation includes a neutral and at least three phases for regulating the electrical current.

According to still further features in the described preferred embodiments, the pulse package of the electrical current is characterized by polarity selected from the group consisting of unipolar pulses and bipolar pulses, the unipolar pulses being a sequence of the pulses of identical shape and of same sign, the bipolar pulses being a sequence of the pulses of identical shape and of alternating sign, and the shape of the pulses is selected from the group consisting of triangular, rectangular, and sinusoidal.

According to still further features in the described preferred embodiments, the mechanism for electrifying the mixture by transmitting into the mixture the at least one series of the at least two cycles of the at least one pulse package and the at least one pause of the electrical current includes at least two electrodes, each of the at least two electrodes is positioned inside each of the at least one processor unit.

According to still further features in the described preferred embodiments, the processor assembly is configured and operates according to a mode selected from the group consisting of batch and continuous, such that the mixture enters, is electrified by the electrical current, and exits the processor assembly including at least one processor unit.

According to still further features in the described preferred embodiments, the extract filtration unit includes a filter medium having a pore size less than 200 microns through which the mixture is filtered.

According to another aspect of the present invention, there is provided an apparatus for electrical extraction of intracellular matter from biological matter, the apparatus comprising a processor assembly including at least one processor unit including a mechanism for electrifying the biological matter by transmitting at least one series of at least two cycles of electrical current, each of the at least two cycles including at least one pulse package of the current and at least one pause of the current, into the biological matter, such that the intracellular matter is released from the biological matter.

According to still further features in the described preferred embodiments, each of the at least two cycles of the at least one pulse package and the at least one pause of the electrical current is characterized by at least one of the following parameters: (i) density of the electrical current is in a range of between about $10^2$ to about $10^4$ $A/m^2$; (ii) field strength of the electrical current is in a range of between about $10^2$ to about $10^4$ V/m; (iii) voltage time derivative of the electrical current is in a range of between about $10^6$ to about $10^8$ V/s; (iv) frequency of the electrical current is in a range of between about 10 Hz to about 1 kHz; (v) duration of each pulse package is in a range of between about 1 to about 10 seconds; (vi) duration of each pause is in a range of about 1 second to about 10 seconds; (vii) ratio of the duration of the pulse package to the duration of the pause is in a range of between about 1/1 to about 1/10; (viii) duration of each of the at least two cycles is in a range of between about 2 seconds to about 50 minutes; and (ix) duration of the at least one series of the at least two cycles is in a range of between about 5 seconds to about 60 minutes.

According to still further features in the described preferred embodiments, the mechanism for electrifying the biological matter by transmitting into the biological matter the at least one series of the at least two cycles of the at least one pulse package and the at least one pause of the electrical current includes at least two electrodes, each of the at least two electrodes is positioned inside each of the at least one processor unit.

According to still further features in the described preferred embodiments, the electrical current is generated by a power supply unit and is controlled and modulated by a central control unit operating according to phase-pulse regulation, the phase-pulse regulation includes a neutral and at least three phases for regulating the electrical current.

According to still further features in the described preferred embodiments, the pulse package of the electrical current is characterized by polarity selected from the group consisting of unipolar pulses and bipolar pulses, the unipolar pulses being a sequence of the pulses of identical shape and of same sign, the bipolar pulses being a sequence of the pulses of identical shape and of alternating sign, and the shape of the pulses is selected from the group consisting of triangular, rectangular, and sinusoidal.

According to still further features in the described preferred embodiments, the processor assembly is configured and operates according to a mode selected from the group consisting of batch and continuous, such that the biological matter enters, is electrified by the electrical current, and exits the processor assembly including at least one processor unit.

According to another aspect of the present invention, there is provided an extract comprising intracellular matter electrically extracted from a mixture of biological matter and an electro-conductive liquid by transmitting into the mixture at least one series of at least two cycles of electrical current, each of the at least two cycles including at least one pulse package of the current and at least one pause of the current, such that the intracellular matter is released from the biological matter.

According to still further features in the described preferred embodiments, the extract comprises a liquid fertilizer, whereby the biological matter is selected from the group consisting of solid human compost and solid animal compost.

According to still further features in the described preferred embodiments, the extract comprises a collection of substances, whereby the biological matter is dry plant matter.

According to still further features in the described preferred embodiments, the extract comprises a collection of oils, whereby the biological matter is pulp, the pulp is selected from the group consisting of orange peels, olives, and lavender.

According to still further features in the described preferred embodiments, the extract comprises a collection of oils, whereby the biological matter is animal solids selected from the group consisting of fish solids and poultry solids.

According to still farther features in the described preferred embodiments, the extract comprises a collection of oils, whereby the biological matter is animal fats, said animal fats include poultry fats sludge flotation.

According to another aspect of the present invention, there is provided a process for reducing levels of odor, COD, and BOD in liquid organic sewage including biological matter comprising the step of electrifying the liquid organic sewage by transmitting into the liquid organic sewage at least one series of at least two cycles of electrical current, each of the at least two cycles including at least one pulse package of the current and at least one pause of the current, causing disruption of cells of the biological matter, thereby inactivating the biological matter as a source of the odor, COD, and BOD.

According to still further features in the described preferred embodiments, each of the at least two cycles of the at least one pulse package and the at least one pause of the electrical current is characterized by at least one of the following parameters: (i) density of the electrical current is in a range of between about $10^2$ to about $10^4$ A/m$^2$; (ii) field strength of the electrical current is in a range of between about $10^2$ to about $10^6$ V/m; (iii) voltage time derivative of the electrical current is in a range of between about $10^6$ to about $10^8$ V/s; (iv) frequency of the electrical current is in a range of between about 10 Hz to about 1 kHz; (v) duration of each the pulse package is in a range of between about 1 to about 10 seconds; (vi) duration of each pause is in a range of about 1 second to about 10 seconds; (vii) ratio of the duration of the pulse package to the duration of the pause is in a range of between about 1/1 to about 1/10; (viii) duration of each of the at least two cycles is in a range of between about 2 seconds to about 50 minutes; and (ix) duration of the at least one series of the at least two cycles is in a range of between about 5 seconds to about 60 minutes.

According to still further features in the described preferred embodiments, the electrical current is generated by a power supply unit and is controlled and modulated by a central control unit operating according to phase-pulse regulation, the phase-pulse regulation includes a neutral and at least three phases for regulating the electrical current.

According to still further features in the described preferred embodiments, the pulse package of the electrical current is characterized by polarity selected from the group consisting of unipolar pulses and bipolar pulses, the unipolar pulses being a sequence of the pulses of identical shape and of same sign, the bipolar pulses being a sequence of the pulses of identical shape and of alternating sign, and the shape of the pulses is selected from the group consisting of triangular, rectangular, and sinusoidal.

According to still further features in the described preferred embodiments, the disruption of cells of the biological matter takes place during each pulse package of the electrical current and during each pause of the electrical current.

According to still further features in the described preferred embodiments, each of the at least two cycles of the at l east one pulse package and the at least one pause of the electrical current is transmitted into the liquid organic sewage by a mechanism positioned inside each of at least one processor unit, the at least one processor unit is positioned inside a processor assembly, the electrical current is generated by a power supply unit and the transmission of the electrical current is controlled and modulated by a central control unit in electronic communication with the processor assembly.

According to still further features in the described preferred embodiments, the mechanism for electrifying the biological matter by transmitting into the biological matter at least one series of the at least two cycles of the at least one pulse package and the at least one pause of the electrical current includes at least two electrodes, each of the at least two electrodes is positioned inside each of the at least one processor unit.

According to still further features in the described preferred embodiments, the liquid organic sewage enters, is electrified by the electrical current, and exits a processor assembly including at least one processor unit, whereby the processor assembly is configured and operates according to a mode selected from the group consisting of batch and continuous.

According to another aspect of the present invention, there is provided a system for reducing levels of odor, COD, and BOD in liquid a feed supply unit for forming a feed supply of the liquid organic sewage to be fed into at least one processor unit; (b) a process assembly including the at least one processor unit for receiving the liquid organic sewage, each of the at least one processor unit includes a mechanism for electrifying the liquid organic sewage by transmitting into the liquid organic sewage at least one series of at least two cycles of electrical current, each of the at least two cycles including at least one pulse package of the current and at least one pause of the current, causing disruption of cells of the biological matter, thereby inactivating the biological matter as a source of the odor, COD, and BOD; (c) a central control unit for controlling and modulating the transmitting of the at least one series of the electrical current into the liquid organic sewage; and (d) a power supply unit controlled by the central control unit for generating and supplying the electrical current to the mechanism.

According to still further features in the described preferred embodiments, each of the at least two cycles of the at least one pulse package and the at least one pause of the electrical current is characterized by at least one of the following parameters: (i) density of the electrical current is in a range of between about $10^2$ to about $10^4$ A/m$^2$; (ii) field strength of the electrical current is in a range of between about $10^2$ to about $10^4$ V/m; (iii) voltage time derivative of the electrical current is in a range of between about $10^6$ to about $10^8$ V/s; (iv) frequency of the electrical current is in a range of between about 10 Hz to about 1 kHz; (v) duration of each pulse package is in a range of between about 1 to about 10 seconds; (vi) duration of each pause is in a range of about 1 second to about 10 seconds; (vii) ratio of the duration of the pulse package to the duration of the pause is in a range of between about 1/1 to about 1/10; (viii) duration of each of the at least two cycles is in a range of between about 2 seconds to about 50 minutes; and (ix) duration of the at least one series of the at least two cycles is in a range of between about 5 seconds to about 60 minutes.

According to still further features in the described preferred embodiments, the central control unit operates according to phase-pulse regulation, the phase-pulse regulation includes a neutral and at least three phases for regulating the electrical current.

According to still further features in the described preferred embodiments, the mechanism for electrifying the mixture by transmitting into the liquid organic sewage the at least one series of the at least two cycles of the at least one pulse package and the at least one pause of the electrical current includes at least two electrodes, each of the at least two electrodes is positioned inside each of the at least one processor unit.

According to still further features in the described preferred embodiments, the processor assembly is configured and operates according to a mode selected from the group consisting of batch and continuous, such that the liquid organic sewage enters, is electrified by the electrical current, and exits the processor assembly including at least one processor unit.

According to another aspect of the present invention, there is provided a liquid organic sewage with reduced levels of odor, COD, and BOD comprising liquid organic sewage including biological matter electrified by transmitting into the liquid organic sewage at least one series of at least two cycles of electrical current, each of the at least two cycles includes at least one pulse package of the current and at least one pause of the current, causing disruption of cells of the biological matter of the liquid organic sewage thereby inactivating the biological matter of the liquid organic sewage as a source of the odor, COD, and BOD.

According to further features in the described preferred embodiments, the liquid organic sewage including the biological matter is obtained from raw municipal sewage.

The process and system for electrical extraction of intracellular matter from biological matter of the present invention serve as significant improvements over currently used processes and systems used for obtaining desirable and useful intracellular matter.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
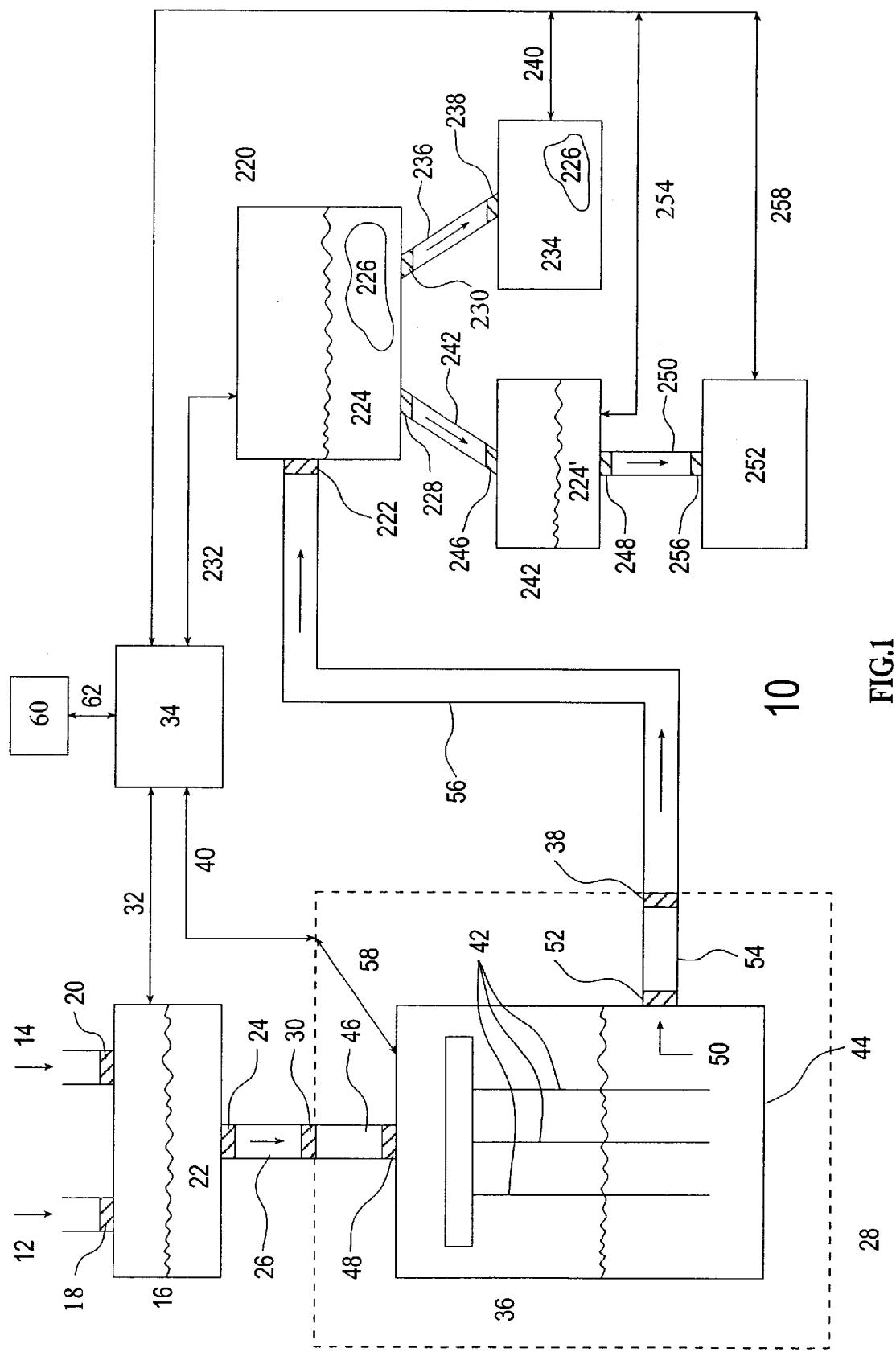
FIG. 1 is a schematic diagram of a preferred embodiment of the system for electrical extraction of intracellular matter from biological matter, according to the teachings of the present invention.

The present invention is of a process and system for electrical extraction of intracellular matter from biological matter, and to extracts obtained by implementing the process and system.

The process and system for electrical extraction of intracellular matter from biological matter of the present invention are based on preparing a mixture of biological matter and an electro-conductive liquid, and electrifying the liquid mixture by transmitting controlled cycles of pulses and pauses of electrical current into the mixture using electrodes, whereby the pulses of electrical current pierce holes into or perforate the cell membranes of the cells, thereby enabling the release of intracellular matter from the cells. Including pauses in each cycle of transmitting electrical current enables firm control of processing conditions, including extent of extraction, temperature effects, and pressure effects, during the electrical extraction process. Extracts so obtained are used for manufacturing a diversity of end products.

It is to be understood that the invention is not limited in its application to the details of construction, arrangement, and composition of the components set forth in the following description, drawings, or examples. The present invention is capable of other embodiments or of being practiced or carried out in various ways. Also, it is to be understood that the phraseology and terminology employed herein are for the purpose of description and should not be regarded as limiting.

Steps, components, operation, and implementation of a process and system for electrical extraction of intracellular matter from biological matter according to the present invention are better understood with reference to the drawings and the accompanying description.

In Step 1 of the process, there is selecting biological matter typically including cellular and non-cellular matter to be used in the feed supply to the processor for electrical extraction. Examples of biological matter suitable for application to the process and system for electrical extraction of the present invention include (i) animal or human compost; (ii) plant matter such as raw, dried, or powdered flowers, seeds, peels, stems, leaves, or roots; (iii) animal solids such as mammal, fish, or poultry solid wastes, for example, internal organs or giblets having substantial amounts of fats and oils, derived from growing farms or processing facilities; and (iv) liquid organic sewage such as raw municipal sewage and related sources of liquid organic waste.

In Step 2, there is preparing a processor feed supply using the selected biological matter of Step 1 for feed to the processor assembly, featuring at least one processor unit, of the electrical extraction system. As processor feed for electrical extraction of intracellular matter, biological matter in at least one of the following or related forms of: animal or human compost; plant matter such as raw, dried, extracted or powdered flowers, roots, stems, peels, seeds, fruits and the like; animal solids such as mammal, fish or poultry solid wastes, for example, internal organs or giblets having substantial amounts of fats and oils, derived from growing farms or processing facilities; and liquid organic sewage, such as raw municipal sewage and related sources of liquid organic waste, is mixed with an electro-conductive liquid such as, but not limited to, any combination of water, alcohol, and glycerin, to a volume ratio in a range of between about 1/1 to about 1/100, preferably about 1/10, volume biological matter/volume electro-conductive liquid. Feed and feed mixing conditions, rates, and parameters entering, inside of, and exiting a feed supply unit are controlled and set by a central control unit in communication with other system units via control/data links.

In Step 3, there is electrifying the processor feed of Step 2, featuring the mixture of biological matter in an electro-conductive liquid, with a series of at least two complete cycles of pulses and pauses of electrical current by activation of electrodes housed in at least one processor unit which is part of a larger processor assembly. One complete cycle of pulses and a pause is herein defined as including at least one pulse package of a pre-determined duration and at least one pause of a pre-determined duration, where a pulse package is the number of pulses of electrical current having a pre-determined pulse frequency, or pulses per second, continuously or discontinuously, transmitted to the biological matter for a pre-determined duration or time interval, and one pause is the duration or time interval during which pulses of electrical current are paused or not transmitted to the biological matter immediately following a pulse package.

For example, one cycle of pulses and a pause may feature a pulse package of 1 second, wherein, the biological matter is exposed to pulses of electrical current having an exemplary pre-determined pulse frequency of 500 pulses per second, for 1 second, immediately followed by a pause of 5 seconds where the biological matter is not exposed to any pulse for 5 seconds immediately following the pulse package of 1 second. Using the same parameters, one series of two cycles of pulses and pauses would then feature the sequence of a pulse package of 1 second, immediately followed by a pause of 5 seconds, immediately followed by a pulse package of 1 second, immediately followed by a second pause of 5 seconds.

For a given cycle of a pulse package and a pause, a pulse package/pause ratio is defined, accordingly, as the ratio of pulse package duration to pause duration. For the preceding example, the pulse package/pause ratio is 1/5. Furthermore, each cycle of a pulse package and a pause can be characterized by the parameter of 'cycle time', defined as the sum of the pulse package duration plus the pause duration. In the above example, the cycle time is 6 seconds, obtained from the sum of pulse package duration of 1 second and pause duration of 5 seconds.

The parameter, 'treatment time', is defined as the total time the processor feed of the selected biological matter is subjected to a series of at least two cycles of pulse packages and pauses. As such, for the process featuring a constant cycle time, the treatment time is simply the cycle time, multiplied by the number of cycles. For example, for the electrical extraction process featuring two cycles, where each cycle includes a pulse package of 1 second, and a pause of 5 seconds, the treatment time is equal to (6 seconds per cycle)×(2 cycles), or 12 seconds. In this example, the biological matter is subjected to electrical extraction for a total time of 12 seconds, with an exposure time to the transmitted pulses of electrical current of 2 seconds, corresponding to two pulse packages of 1 second each, and a non-exposure time of 10 seconds, corresponding to two pauses of 5 seconds each, during a two cycle treatment time of 12 seconds.

As another illustrative example of treatment time, for the same electrical extraction process featuring four, instead of two, cycles, of pulse package duration of 1 second and pause duration of 5 seconds, the series of four cycles features the sequence of: pulse of 1 second, pause of 5 seconds, first cycle completion at 6 seconds, pulse of 1 second, pause of 5 seconds, second cycle completion at 12 seconds, pulse of 1 second, pause of 5 seconds, third cycle completion at 18 seconds, and pulse of 1 second, pause of 5 seconds, fourth and final cycle completion at 24 seconds, for a treatment time of 24 seconds. In this example, the biological matter is exposed to pulses of electrical current for a total of 4 seconds, and was not exposed to pulses of electrical current for a total of 20 seconds.

Exposing the biological matter to pre-determined cycles of pulse packages of electrical current and pauses of no electrical current enables firm control of conditions taking place inside the processor zone, at the surface of the biological matter, and inside of the biological matter, especially with respect to product profile or extent of processing, temperature profile and thermal effects relating to distribution, extent, and rate of heat generation or consumption, and pressure effects relating to distribution, extent, and rate of pressure generation or consumption, during the electrical extraction process. It was found that simply transmitting continuous, non-cycled, pulse packages of electrical current to the biological matter caused excessive heat and/or pressure generation to the extent of boiling and/or pressure build-up of the processor feed contents. Clearly, such phenomena potentially leads to uncontrolled processor and processing conditions, which could be detrimental to the yield and extent of the final extracts, and therefore, it was determined that time intervals of non-exposure of the biological matter to the pulses were necessary in order to enable firm control of processor, and thereafter, processing conditions during the electrical extraction process.

Electrical power supplied to the electrodes used for transmitting the pulsed electrical current to the liquid mixture of biological matter, electrifying the liquid mixture and perforating the cells, thereby enabling the release of intracellular matter, is generated and highly controlled with respect to polarity, shape or waveform, magnitude or amplitude, and duration, by a specially designed power supply unit in electronic communication with the central control unit.

The power supply unit operates according to control of the above described parameters relating to pulses and pauses of the electrical current, including (i) electrical current density in a range of between about $10^2$ to about $10^4$ A/m$^2$, (ii) electric field strength in a range of between about $10^2$ to about $10^4$ V/m, (iii) voltage time derivative or steepness in a range of between about $10^6$ to about $10^8$ V/s, (iv) pulse frequency, in terms of pulses per second, in a range of between about 10 Hz to about 1 kHz, (v) pulse package duration in a range of between about 1 to about 10 seconds, where pulse package duration refers to the duration the mixture of biological matter is exposed to the transmitted pulses, (vi) pause duration in a range of about 1 second to about 10 seconds, where pause duration refers to duration or time interval the mixture of biological matter is not exposed to pulses immediately following transmission of a pulse package, (vii) pulse package/pause ratio in a range of between about 1/1 to about 1/10, where pulse package/pause ratio is the ratio of pulse package duration to pause duration, (viii) cycle time in a range of between about 2 seconds to about 50 minutes, where cycle time is the sum of pulse package duration and pause duration, and (ix) treatment time in a range of between about 5 seconds to about 60 minutes, where treatment time is the total time the processor feed of the selected biological matter is subjected to a series of at least two cycles of pulse packages and pauses.

The pulses of electrical current can be characterized as either unipolar or bipolar. Unipolar pulses are a sequence of pulses of electrical voltage of identical shape or waveform and of the same sign, positive or negative. Bipolar pulses are a sequence of pulses of electrical voltage of identical shape or waveform and of alternating sign, Pulses, unipolar or bipolar, can be of different shapes or waveforms, such as triangular, rectangular, sinusoidal, and so on.

As a result of transmission of pulses of electrical current to the feed mixture inside a processor unit, the feed mixture undergoes dynamic heat and mass transfer effects, and in some cases boiling of the liquid feed mixture takes place. Extent of heating and pressurization of the feed mixture, during electrification by the electrodes, is monitored and controlled by modulating and setting the above described system parameters by the central control unit. Optional liquid heat exchanger and/or pressure regulating equipment may be included as part of the processor assembly, for additional temperature and/or pressure control of the mixture of biological matter during processing conditions. The processor assembly, including at least one processor unit featuring the electrodes, is in electronic communication with the central control unit and the power supply unit via control/data links.

For selected construction of the processor assembly used in agricultural applications of electrical extraction of human or animal compost for forming liquid fertilizer, described and illustrated in FIGS. 2 through 4, and in Example 1 below, agricultural 'demand' elements such as metals iron and zinc, may be supplied to the processor feed while the processor feed is in the processor unit, by placing a second set of dissolvable electrodes including these elements in the processing zone.

In this way, the processor effluent, and ultimately, the extract product is automatically enriched with 'demand' elements.

In Step 4, there is mechanically separating the processor effluent. A separator unit mechanically separates the processor effluent into liquid extract and solids, where the extract includes the intracellular matter. The separator unit is in electronic communication with the central control unit via control/data links.

In Step 5, there is filtering of the extract. Preferably a sieve or equivalent type of filtration device is used for filtering the extract. Inside an extract filtration unit, the extract is filtered or sieved, preferably through a filtration medium or sieves having filter pore or sieve size of about 120 microns. This filtration step enables removal of undesirable particles and other relatively large size impurities from the extract. The extract filtration unit is in electronic communication with the central control unit via control/data links.

In Step 6, there is separate collecting of solids and extract. Solids are collected in a solids collection unit and are either discarded or are further processed by another system such as a solids waste processing system. Extract is collected in an extract collection unit. The solids collection unit and extract collection unit are each in electronic communication with the central control unit via control/data links.

Examples of obtained intracellular matter extracts, corresponding to applying electrical extraction to the above examples of selected biological matter raw materials listed in Step 1, include (i) highly concentrated liquid fertilizer, including valuable elements and nutrients such as nitrogen, phosphorous, potassium, and their oxides, from animal or human compost; (ii) valuable substances derived from plant matter; (iii) oils from plant matter; and (iv) fats and oils from animal solids such as fish or poultry solids. These intracellular matter extracts, in turn, are used as raw materials for manufacturing end products such as fertilizers, medicines, cosmetics, food flavorings and spices, in the agricultural, pharmaceutical, cosmetic, and food industries. The process and system according to the present invention can be used also to extract intracellular matter from bacteria present in liquid organic sewage, thereby neutralizing such bacteria, and reducing undesirable levels of chemical oxygen demand (COD), biological oxygen demand (BOD), and odor characterizing liquid organic sewage. Such liquid organic sewage may either come in contact with, or be used for, recycling into drinking or commercial water supplies.

The mechanism of electrically extracting intracellular matter from biological matter is based on a combination of electrical and thermal convection processes forcing intracellular matter out from the cells. The intracellular matter serves as a matrix or vehicle for movement and subsequent separation of the target extracts from the rest of the system feed of biological matter which includes cellular and non-cellular matter. The electrical pulses destroy colloidal particles and change electrical charges of particle components, causing coagulation of particle components into larger sized colloidal particles. The larger sized colloidal particles form sediment, either by themselves or by external addition of flocculates. Undesirable and unneeded sediment is separated from the liquids extract featuring the target extracts.

The system for electrical extraction of intracellular matter from biological matter is now described. An electrical extraction system is provided, including (a) a feed supply unit; (b) a processor assembly including at least one processor unit featuring a set of at least two electrodes; (c) a central control unit; (d) a liquids/solids separator unit; (e) an extract filtration unit; (f) an extract collection unit and a solids collection unit; and (g) control/data links enabling independent and/or synchronized electronic communication among the various system units and the central control unit.

Electrical extraction system 10 is shown in FIG. 1, a schematic diagram of a preferred embodiment of the system for electrical extraction of intracellular matter from biological matter. Selected biological matter 12 and an electro-conductive liquid 14 are separately fed into feed supply unit 16, via feed supply inlet units 18 and 20, respectively, and are mixed forming liquid feed 22. Feed supply inlet units 18 and 20, and other inlet and outlet units, positioned between the various units and components of system 10 schematically illustrated in FIG. 1, indicated in the following description, include mechanical and electronic equipment and mechanisms such as conduits, valves, connectors, and electronic controls, necessary for transporting, mixing, and controlling flow between the indicated units. Feed 22 exits feed supply unit 16 via feed supply outlet unit 24, flows through conduit 26 and enters processor assembly 28 via processor assembly inlet unit 30. Feed and mixing conditions, rates, and parameters entering, inside of, and exiting feed supply unit 16, are controlled and set via control/data links 32 in communication with central control unit 34.

Processor assembly 28 including at least one processor unit 36, includes processor assembly inlet unit 30 and processor assembly outlet unit 38 for entering and exiting of feed 22, respectively. In an alternative embodiment of the system of the present invention, processor assembly 28 includes a multiple of processor units (not shown), along with appropriate mechanical and electrical equipment and mechanisms enabling connection and communication for fluid transport, mixing, and electronic control among the processor units and with central control unit 34. Control/data links 40 enable electronic communication between processor assembly 28 and central control unit 34.

Processor unit 36 features a set of at least two electrodes 42 necessary for enabling implementation of this invention. Processor unit 36 includes processor unit housing 44, and receives feed 22 through conduit 46 via processor inlet unit 48. In general, processor unit volume is in the range of about 0.1 liter to about 1,000 liters, and processor unit characteristic size, such as a diameter, is in the range of about 0.05 meter to about 1 meter. Processor unit 36 is preferably made from metal such as black iron, or from plastic such as PVC, and electrodes 42 are preferably made from a steel such as 316 stainless steel. Typical dimensions of electrodes 42 are from about 0.04 m×0.1 m×0.001 m to about 1 m×1.5 m×0.006 m.

Following electrification of feed 22, caused by activation of electrodes 42, processor effluent 50 exits processor unit 36 via processor outlet unit 52 through conduit 54, then exits processor assembly unit 28 via processor assembly outlet unit 38 and flows into conduit 56. Processor unit 36 is in electronic communication with processor assembly 28 and with central control unit 34 via control/data links 58 and 40.

Central control unit 34 enables centralized, individual and/or synchronized control of the various units of system 10, and is used for modulating and transferring electrical power from a power supply unit 60. Central control unit 34 is in electronic communication with each of the individual units of system 10, feed supply unit 16, processor assembly 28, at least one processor unit 36, separator unit 220, solids collection unit 234, extract filtration unit 242, extract collection unit 252, and power supply unit 60, via control/data links 32, 40, 58, 232, 240, 254, 258, and 62, respectively. Power supply unit 60 is capable of operating according to multiple phase electrical power, for example, including three phases or five phases of electrical power.

Electrical power supplied to electrodes 42 used for transmitting series of cycles of pulsed and paused electrical current through feed 22 of the liquid mixture, thereby electrifying the liquid mixture and perforating cells present therein, is generated and highly controlled with respect to shape or form, polarity, and magnitude or amplitude, by a specially designed power supply unit 60, operating according to modulation and control, by central control unit 34.

Power supply unit 60 operates according to control of the previously described and exemplified parameters relating to pulses and pauses of the electrical current, including (i) electrical current density in a range of between about $10^2$ to about $10^4$ A/m$^2$, (ii) electric field strength in a range of between about $10^2$ to about $10^4$ V/m, (iii) voltage time derivative or steepness in a range of between about $10^6$ to about $10^8$ V/s, (iv) pulse frequency, in terms of pulses per second, in a range of between about 10 Hz to about 1 kHz, (v) pulse package duration in a range of between about 1 to about 10 seconds, (vi) pause duration in a range of about 1 second to about 10 seconds, (vii) pulse package/pause ratio in a range of between about 1/1 to about 1/10, (viii) cycle time in a range of between about 2 seconds to about 50 minutes, and (ix) treatment time in a range of between about 5 seconds to about 60 minutes.

Central control unit 34 includes a mechanism based on phase-pulse regulation, for example, a solid state relay mechanism (not shown). Regulation by the solid state relay provides the capability of generating packages of unipolar or bipolar pulses of electrical current. Unipolar pulses are a sequence of pulses of electrical voltage of identical shape or waveform and of the same sign, positive or negative. Bipolar pulses are a sequence of pulses of electrical voltage of identical shape or waveform and of alternating sign. Pulses, unipolar or bipolar, can be generated as featuring different shapes or waveforms, such as triangular, rectangular, sinusoidal, and so on.

Figure 2A:
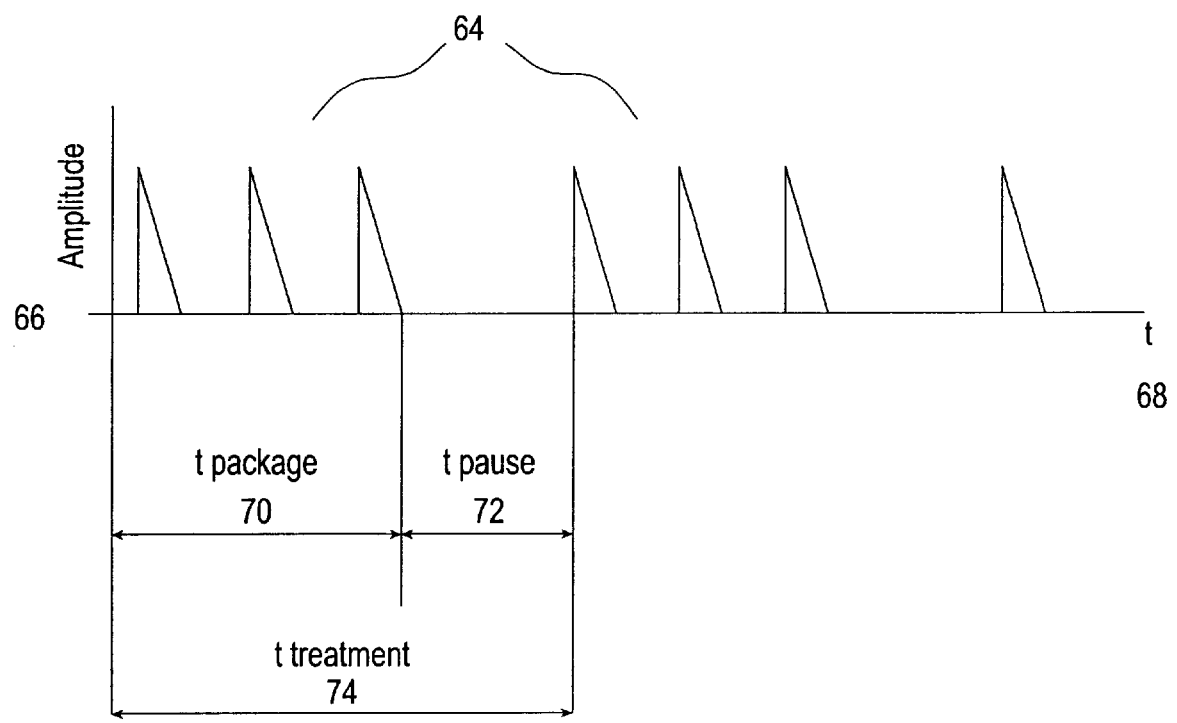
FIG. 2A is an illustration of a unipolar triangular waveform and selected parameters of the pulsed electrical current generated by a power supply unit and modulated by a central control unit, according to the present invention.

FIG. 2A is an illustration of a unipolar triangular waveform and selected parameters of the cycled pulsed and paused electrical current generated by power supply unit 60 and modulated by central control unit 34. In FIG. 2A, unipolar triangular waveform 64 is shown as a plot of amplitude 66 as a function of time 68, and illustrates the parameters of $t_{package}$ 70, $t_{pause}$ 72, and $t_{treatment}$ 74. The solid state relay mechanism periodically interrupts the electrical current, thus forming packages of pre-determined durations or time intervals of pulses and pauses of electrical current. For example, section 70 of $t_{package}$, shows a pulse frequency, described by parameter (iv) above, of a single pulse package duration or time interval, as part of a single pulse/pause cycle, described by parameter (viii) above. Section 72 of $t_{pause}$ shows a pause duration or time interval, described by parameter (vi) above, as part of a single pulse/pause cycle. The ratio $t_{package}/t_{pause}$, corresponds to the ratio of pulse package duration to pause duration, described by parameter (vii) above. Section 74 of $t_{treatment}$ shows one complete cycle of a pulse package duration plus a pause duration.

Figure 2B:
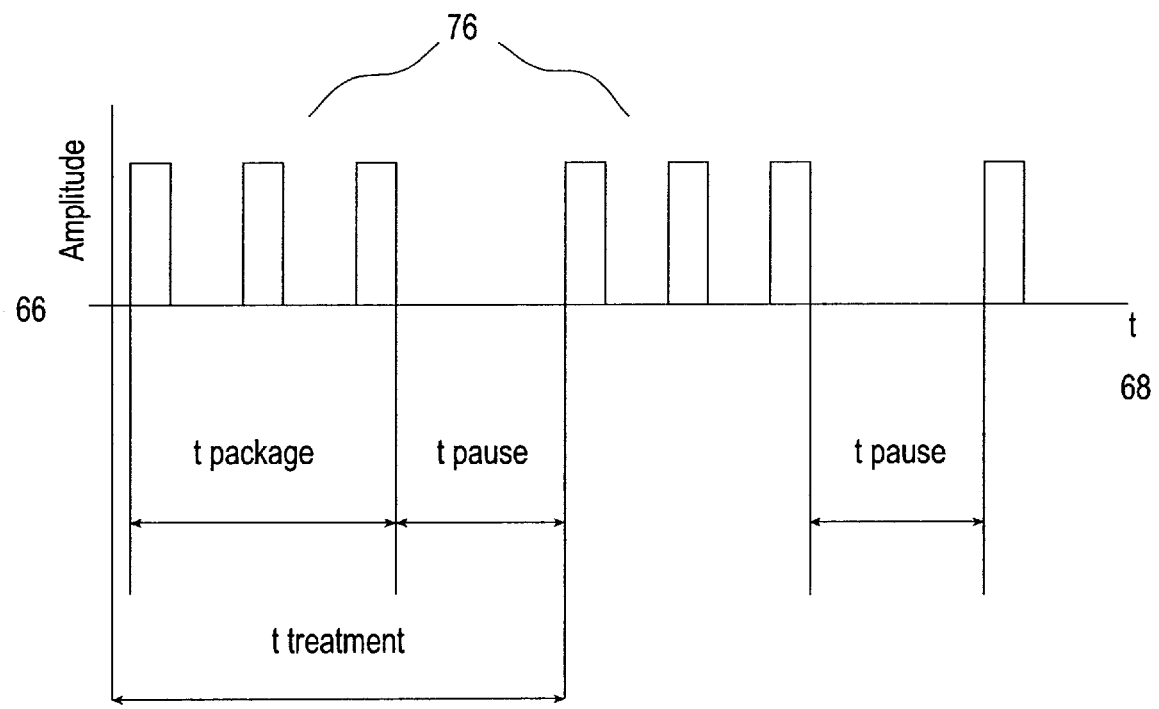
FIG. 2B is an illustration of a unipolar rectangular waveform and selected parameters of the pulsed electrical current generated by a power supply unit and modulated by a central control unit, according to the present invention.

FIG. 2B is an illustration of a unipolar rectangular waveform and selected parameters of the cycled pulsed and paused electrical current generated by power supply unit 60 and modulated by central control unit 34, wherein unipolar rectangular waveform 76 is shown as a plot of amplitude 66 as a function of time 68, and illustrates the parameters of $t_{package}$, $t_{pause}$, and $t_{treatment}$.

Figure 2C:
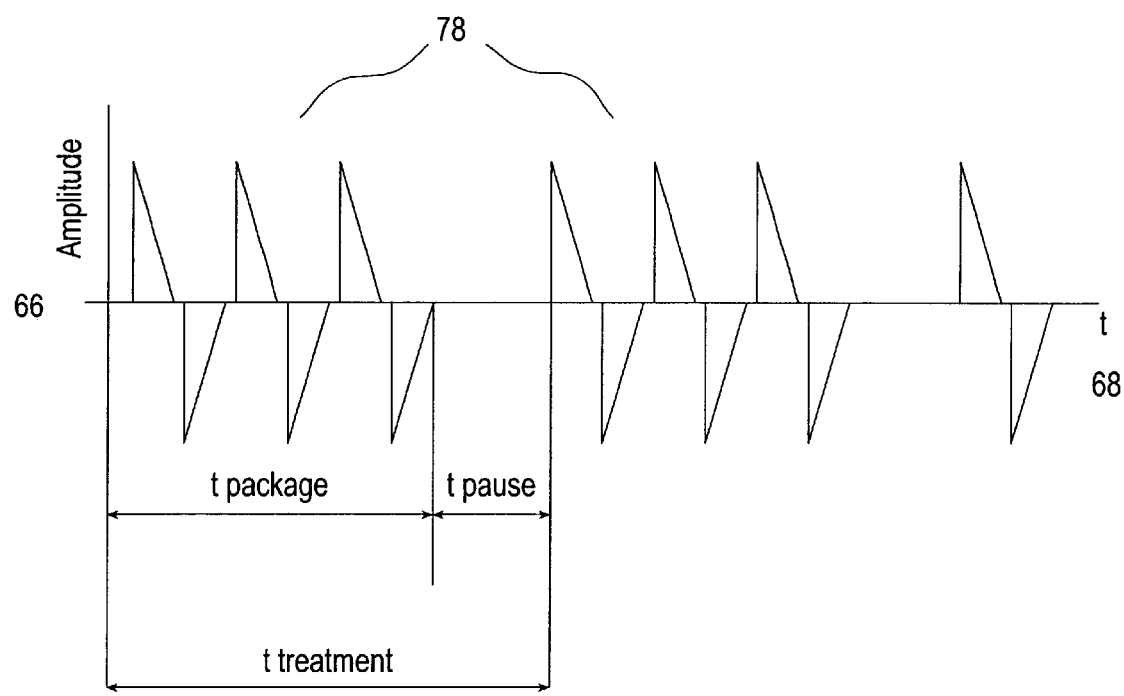
FIG. 2C is an illustration of a bipolar triangular waveform and selected parameters of the pulsed electrical current generated by a power supply unit and modulated by a central control unit, according to the present invention.

FIG. 2C is an illustration of a bipolar triangular waveform and selected parameters of the pulsed electrical current generated by power supply unit 60 and modulated by central control unit 34, wherein bipolar triangular waveform 78 is shown as a plot of amplitude 66 as a function of time 68, and illustrates the parameters of $t_{package}$, $t_{pause}$, and $t_{treatment}$.

Figure 2D:
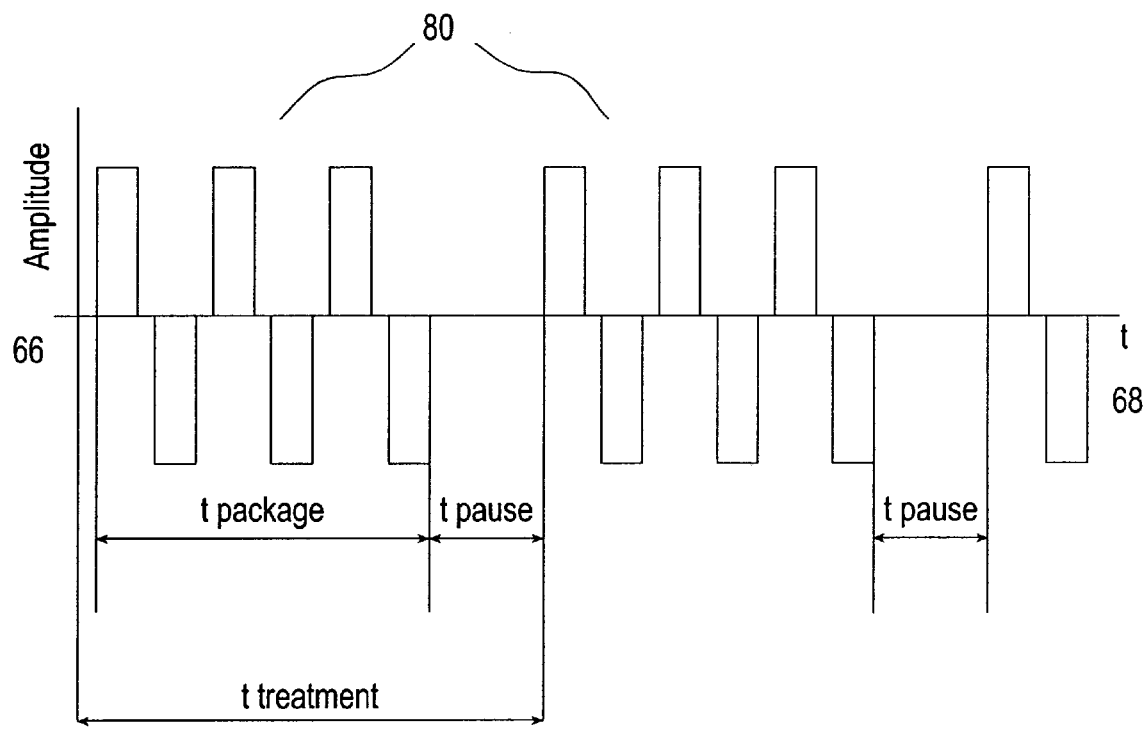
FIG. 2D is an illustration of a bipolar rectangular waveform and selected parameters of the pulsed electrical current generated by a power supply unit and modulated by a central control unit, according to the present invention.

FIG. 2D is an illustration of a bipolar rectangular waveform and selected parameters of the pulsed electrical current generated by power supply unit 60 and modulated by central control unit 34, wherein bipolar rectangular waveform 80 is shown as a plot of amplitude 66 as a function of time 68, and illustrates the parameters of $t_{package}$, $t_{pause}$, and $t_{treatment}$.

Processor assembly 28 including at least one pro unit may be configured to operate in either a batch mode or in a continuous mode. For processor assembly 28 including multiple processor units, appropriate mechanical and electrical equipment and mechanisms enabling connection and communication for fluid transport, mixing, and electronic control among the processor units and with central control unit 34 are included. FIGS. 3 through 7 illustrate alternative embodiments of processor assembly 28, which in general, can be used for electrical extraction of the variety of biological matter described above.

Figure 3A:
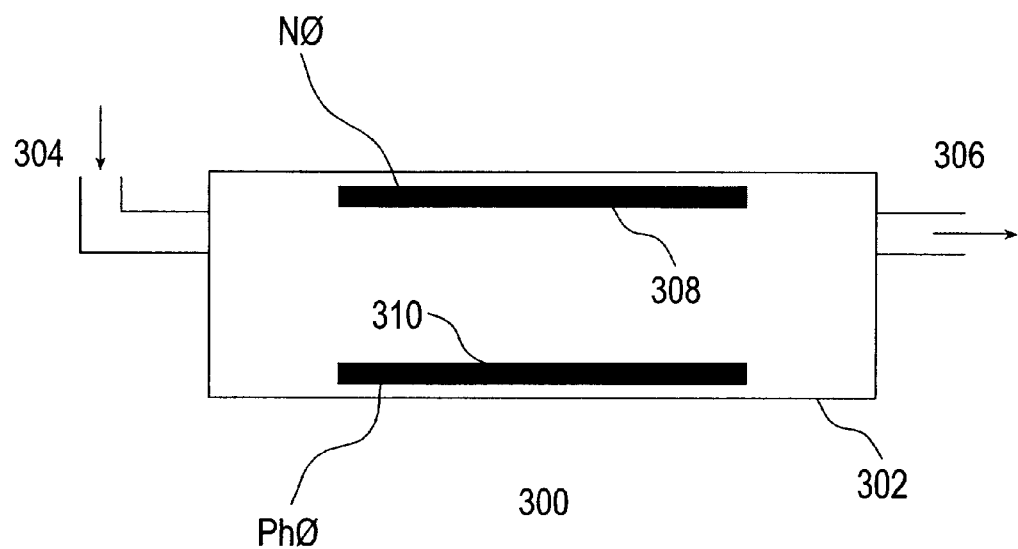
FIG. 3A is a schematic diagram of a first preferred embodiment of a batch mode processor assembly of the electrical extraction system shown in FIG. 1.

FIG. 3A is a schematic diagram of a first preferred embodiment of a batch mode processor assembly of the electrical extraction system shown in FIG. 1. In FIG. 3A, processor assembly 28 (FIG. 1) features a single processor unit 300 which includes processor unit housing 302, processor inlet unit 304, processor outlet unit 306, and one set of two electrodes 308 and 310. By way of central control unit 34, the electrodes are connected and operate according to single phase electrical power generated by power supply unit 60. Electrode 308 is connected to neutral, and electrode 310 is connected to phase.

Figure 3B:
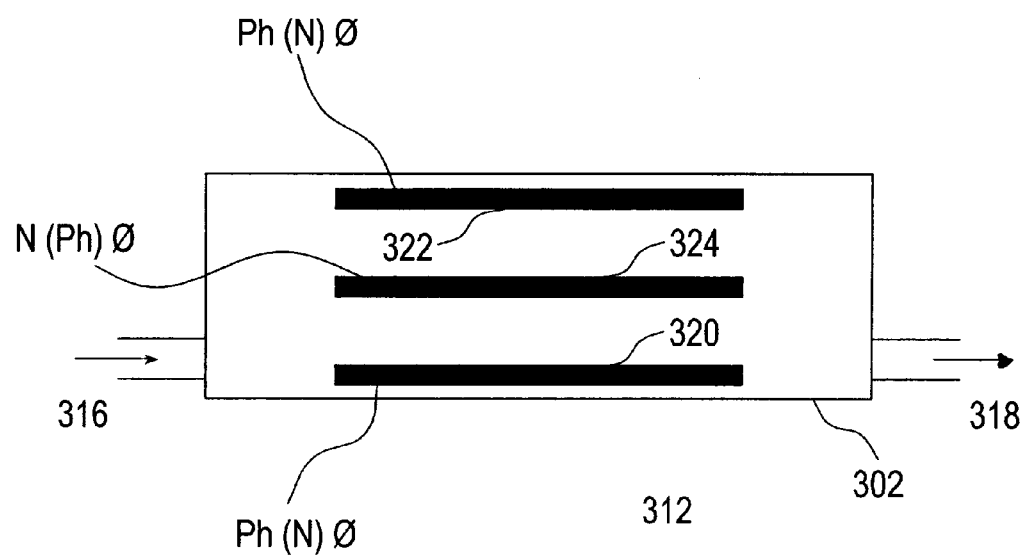
FIG. 3B is a schematic diagram of a second preferred embodiment of a batch mode processor assembly of the electrical extraction system shown in FIG. 1.

FIG. 3B is a schematic diagram of a second preferred embodiment of a batch mode processor assembly of the electrical extraction system shown in FIG. 1. In FIG. 3B, processor assembly 28 (FIG. 1) features a single processor unit 312 which includes processor unit housing 314, processor inlet unit 316, processor outlet unit 318, and one set of three electrodes 320, 322, and 324. By way of central control unit 34, the electrodes are connected and operate according to single phase electrical power generated by power supply unit 60. Outer electrodes 320 and 322 are connected to phase, and middle electrode 324 is connected to neutral.

Figure 3C:
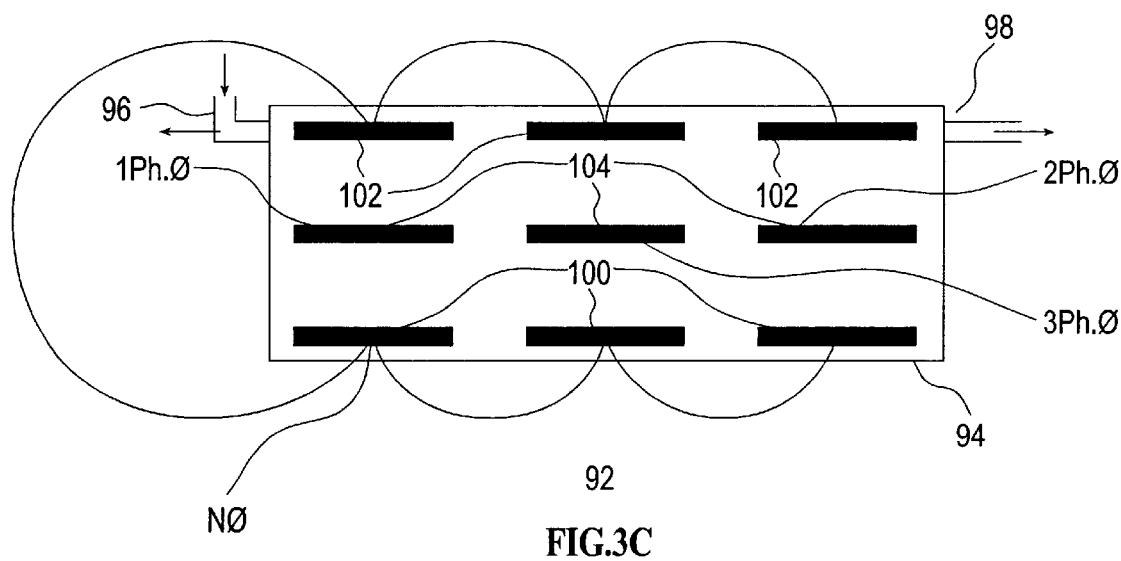
FIG. 3C is a schematic diagram of a third preferred embodiment of a batch mode processor assembly of the electrical extraction system shown in FIG. 1.

FIG. 3C is a schematic diagram of a third preferred embodiment of a batch mode processor assembly of the electrical extraction system shown in FIG. 1. In FIG. 3C, processor assembly 28 (FIG. 1) features a single processor unit 92 which includes processor unit housing 94, processor inlet unit 96, processor outlet unit 98, and three sets of three electrodes 100, 102, and 104. By way of central control unit 34, the electrodes are connected and operate according to three phase electrical power generated by power supply unit 60. Outer electrode sets 100 and 102 are connected to neutral, and middle electrode set 104 is connected to phase.

Figure 3D:
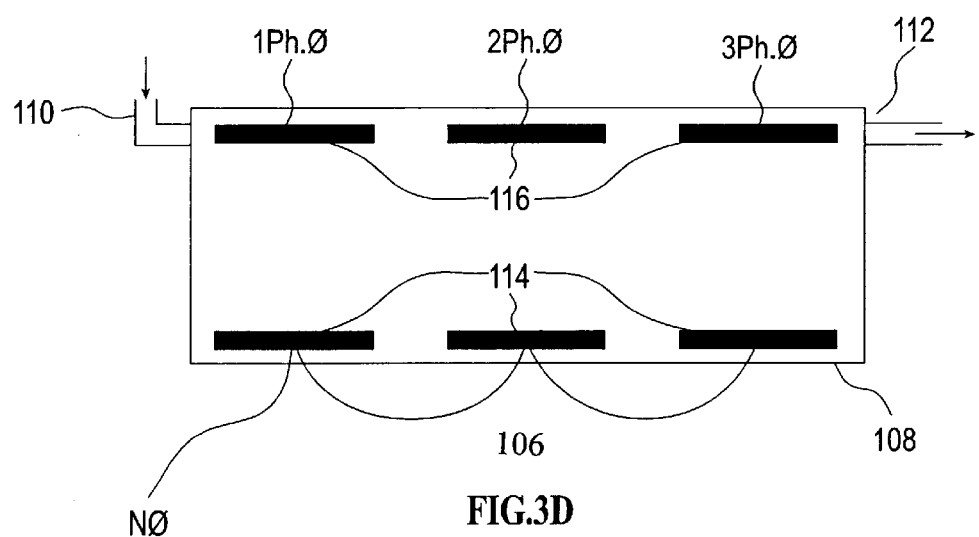
FIG. 3D is a schematic diagram of a fourth preferred embodiment of a batch mode processor assembly of the electrical extraction system shown in FIG. 1.

FIG. 3D is a schematic diagram of a fourth preferred embodiment of a batch mode processor assembly of the electrical extraction system shown in FIG. 1. In FIG. 3D, processor assembly 28 (FIG. 1) features a single processor unit 106 which includes processor unit housing 108, processor inlet unit 110, processor outlet unit 112, and two sets of three electrodes 114 and 116. By way of central control unit 34, the electrodes are connected and operate according to three phase electrical power generated by power supply unit 60. First electrode set 114 is connected to a neutral, and second electrode set 116 is connected to phase.

Figure 3E:
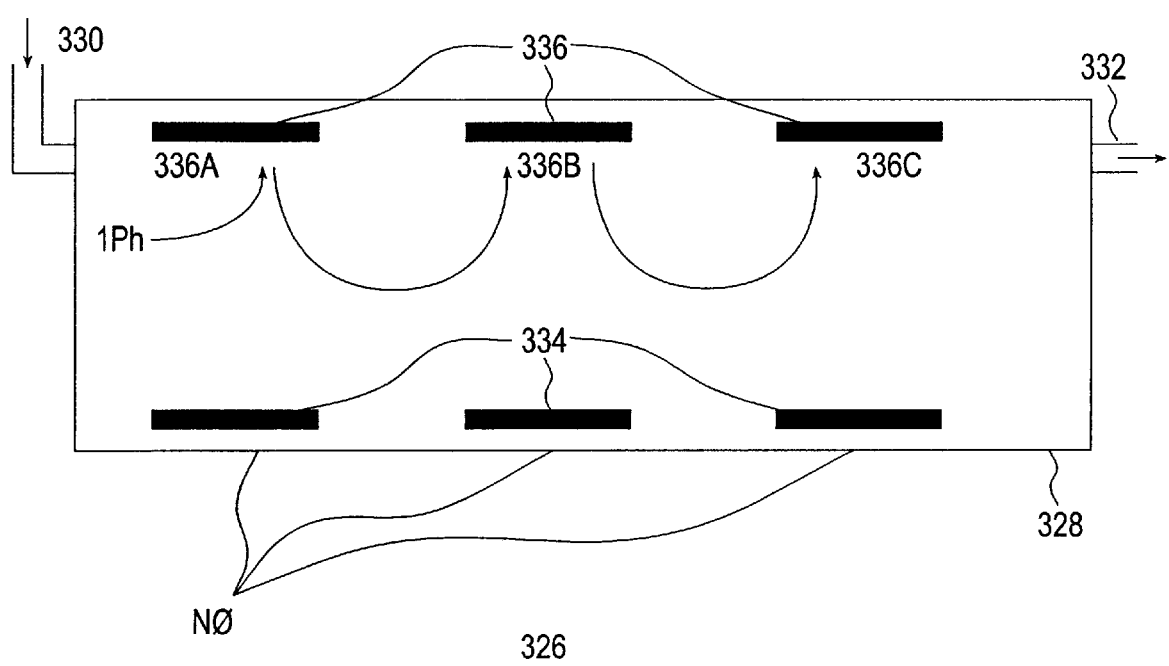
FIG. 3E is a schematic diagram of a fifth preferred embodiment of a batch mode processor assembly of the electrical extraction system shown in FIG. 1.

FIG. 3E is a schematic diagram of a fifth preferred embodiment of a batch mode processor assembly of the electrical extraction system shown in FIG. 1. In FIG. 3E, processor assembly 28 (FIG. 1) features a single processor unit 326 which includes processor unit housing 328, processor inlet unit 330, processor outlet unit 332, and two sets of three electrodes 334 and 336. By way of central control unit 34, the electrodes are connected and operate according to single phase electrical power generated by power supply unit 60. First electrode set 3 is connected to a neutral, and second electrode set 336 is connected to phase, whereby the phase is running along second electrode set 336 from first electrode 336A to second electrode 336B to third electrode 336C.

Figure 4A:
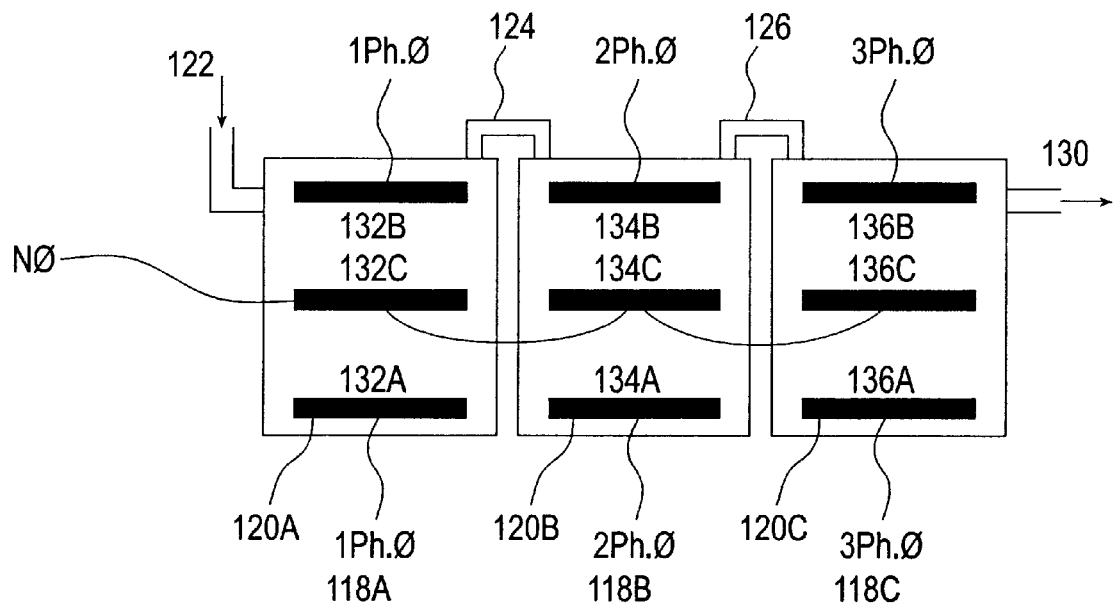
FIG. 4A is a schematic diagram of a sixth preferred embodiment of a batch mode processor assembly of the electrical extraction system shown in FIG. 1.

FIG. 4A is a schematic diagram of a sixth preferred embodiment of a batch mode processor assembly of the electrical extraction system shown in FIG. 1. In FIG. 4A, processor assembly 28 (FIG. 1) features three interconnected processor units 118A, 118B, and 118C, which include processor unit housings 120A, 120B, and 120C, respectively, processor inlet unit 122, processor interconnecting units 124 and 126, and processor outlet unit 130, wherein each processor unit has a set of three electrodes. By way of central control unit 34, the electrodes are connected and operate according to three phase electrical power generated by power supply unit 60. In processor units 118A, 118B, and 118C, each of the two outer electrodes 132A and 132B, 134A and 134B, and, 136A and 136B, respectively, is connected to phase, and each middle electrode 132C, 134C, and 136C, respectively, is connected to a neutral.

Figure 4B:
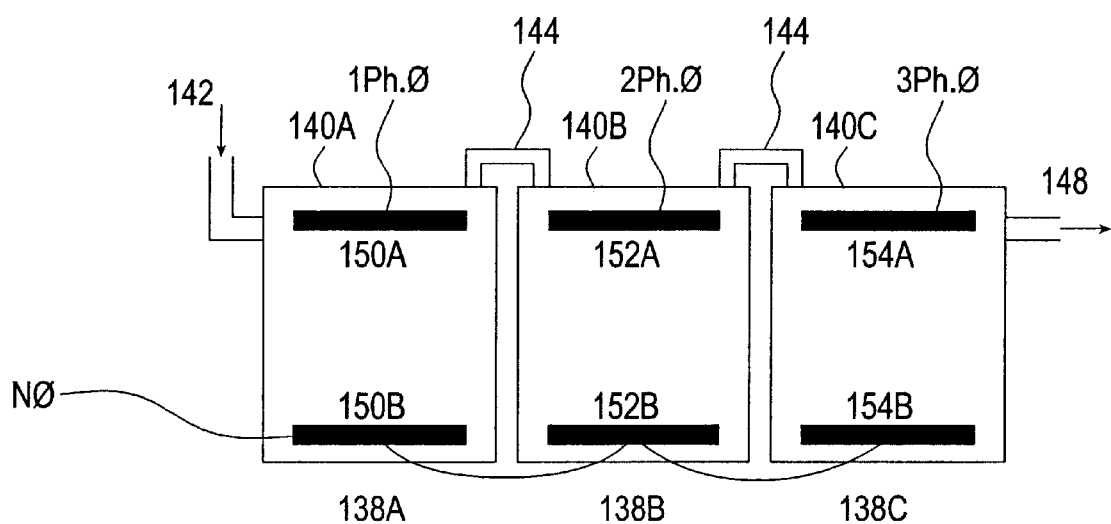
FIG. 4B is a schematic diagram of a seventh preferred embodiment of a batch mode processor assembly of the electrical extraction system shown in FIG. 1.

FIG. 4B is a schematic diagram of a seventh preferred embodiment of a batch mode processor assembly of the electrical extraction system shown in FIG. 1. In FIG. 4B processor assembly 28 (FIG. 1) features three interconnected processor units 138A, 138B, and 138C, which include processor unit housings 140A, 140B, and 140C, respectively, processor inlet unit 142, processor interconnecting units 144 and 146, and processor outlet unit 148, wherein each processor unit has a set of two electrodes. By way of central control unit 34, the electrodes are connected and operate according to three phase electrical power generated by power supply unit 60. In processor units 138A, 138B, and 138C, each outer electrode 150A, 152A, and, 154A, respectively, is connected to phase, and each outer electrode 150B, 152B, and 154B, respectively, is connected to a neutral.

Figure 5A:
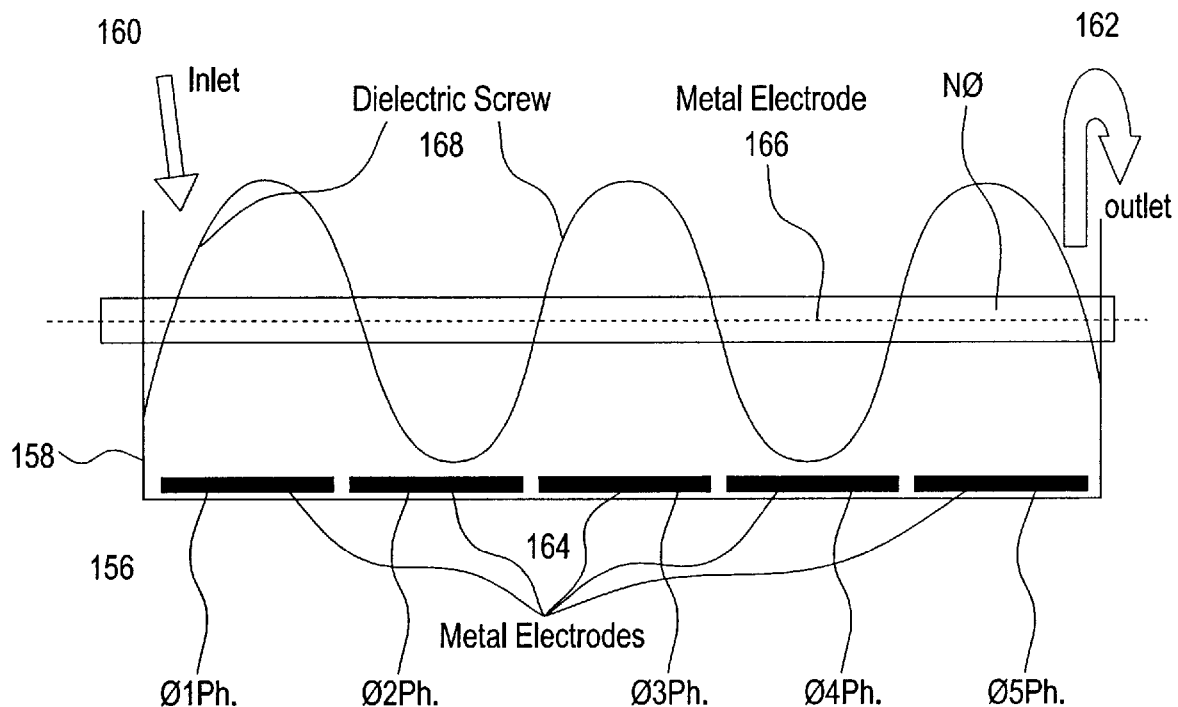
FIG. 5A is a schematic diagram of a preferred embodiment of a continuous mode processor assembly of the electrical extraction system shown in FIG. 1.

FIG. 5A is a schematic diagram of a preferred embodiment of a continuous mode processor assembly of the electrical extraction system shown in FIG. 1. In FIG. 5A, processor assembly 28 (FIG. 1) features a single continuous mode processor unit 156, which includes processor unit housing 158, processor inlet unit 160, processor outlet unit 162, at least one outer electrode, shown here as an exemplary set of five outer electrodes 164, inner metal electrode 166, and dielectric screw 168. Dielectric screw 168 functions to enable transportation of the liquid mixture feed 22 of biological matter and electro-conductive liquid. Dielectric screw 168 is preferably made from plastic. By way of central control unit 34, the electrodes are connected and operate according to one or three phase electrical power generated by power supply unit 60. In processor unit 156, each of the five outer electrodes 164 is connected to phase, and electrode 166 is connected to a neutral. In general, when the number of outer electrodes is more than the number of phases of electrical power, the outer electrodes, for example outer electrodes 164 in processor unit 156, are interconnected.

Figure 5B:
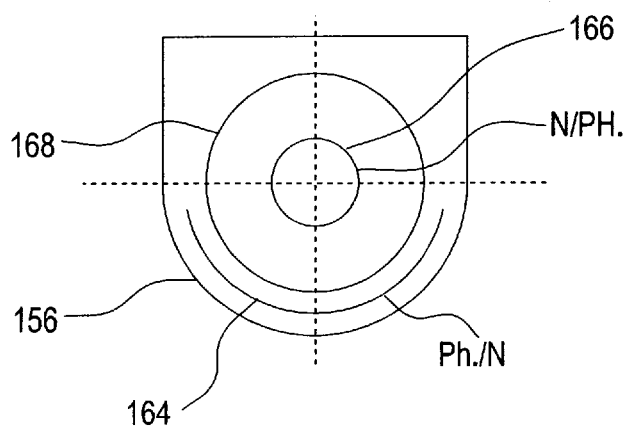
FIG. 5B is a schematic diagram of a top view of the processor assembly shown in FIG. 5A.

FIG. 5B is a schematic diagram of a top view of the preferred embodiment of the continuous mode processor assembly of FIG. 5A, of the electrical extraction system shown in FIG. 1.

Figure 6A:
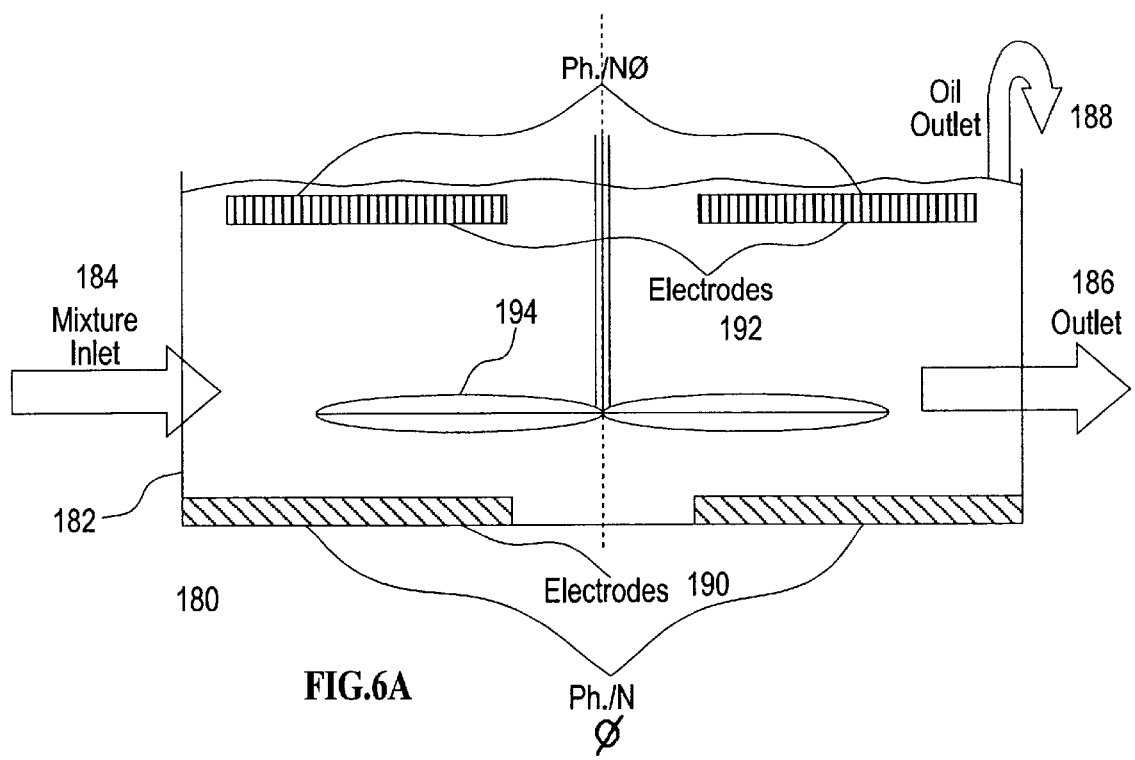
FIG. 6A is a schematic diagram of a side view of an eighth preferred embodiment of a batch mode processor assembly of the electrical extraction system shown in FIG. 1.

FIG. 6A is a schematic diagram of a side view of an eighth preferred embodiment of a batch mode processor assembly of the electrical extraction system shown in FIG. 1. In FIG. 6A, processor assembly 28 (FIG. 1) features a single processor unit 180 which includes processor unit housing 182, processor inlet unit 184, at least two processor outlet units 186 and 188, and two sets of two electrodes 190 and 192. By way of central control unit 34, the electrodes are connected and operate according to multiple phase electrical power generated by power supply unit 60. First electrode set 190 is connected to a neutral, and second electrode set 192 is connected to phase. Mixing of processor feed can be performed either mechanically by including an optional stirrer device 194 or by air, for example by using an air compressor (not shown) for supplying pressurized air into processor unit 180. This processor unit configuration is especially suitable in applications of electrical extraction of fats and oils from biological matter originating from fish or other animal processing facilities. Accordingly, for a feed mixture at a level above top electrode set 192, processor inlet unit 184 can be positioned between electrode sets 190 and 192, while at least one additional processor outlet unit 188 is positioned above top electrode set 192, since specific gravities of oils are, in general, lower than that of water.

Figure 6B:
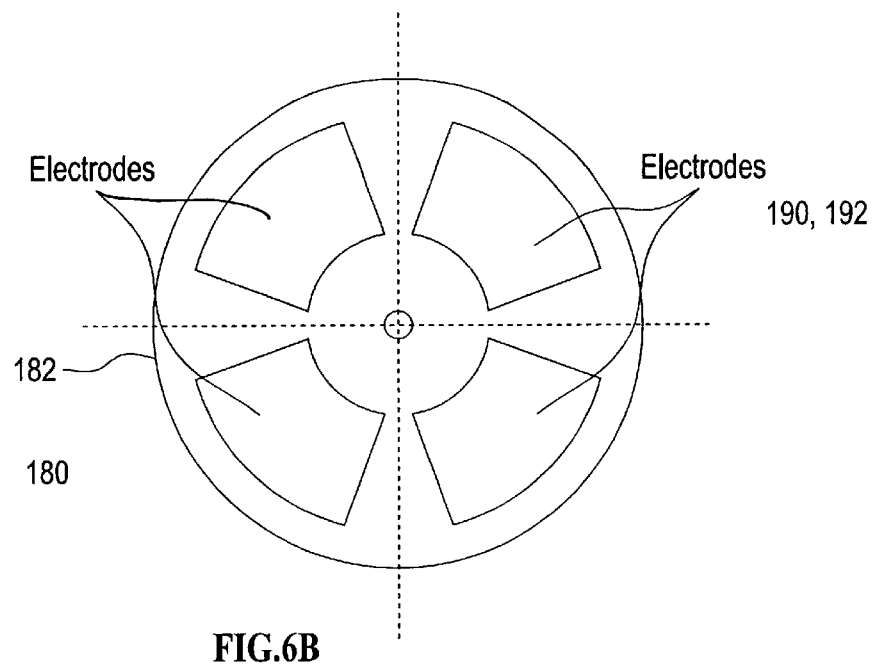
FIG. 6B is a schematic diagram of a top view of the processor assembly shown in FIG. 6A.

FIG. 6B is a schematic diagram of a top view of the preferred embodiment of the batch mode processor assembly of FIG. 6A, of the electrical extraction system shown in FIG. 1.

Figure 7:
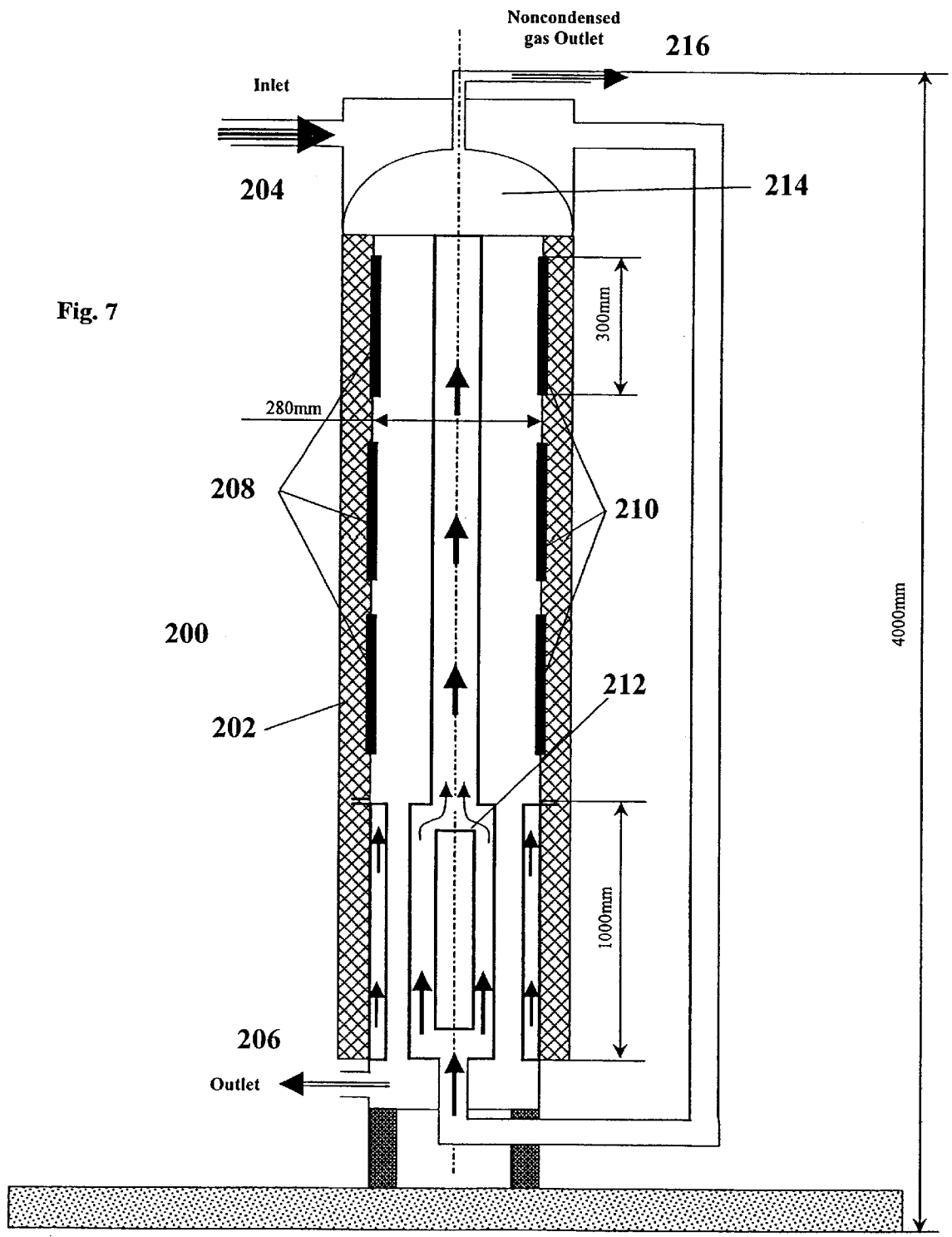
FIG. 7 is a schematic diagram of a second preferred embodiment of a continuous mode processor assembly of the electrical extraction system shown in FIG. 1.

FIG. 7 is a schematic diagram of a second preferred embodiment of a continuous mode processor assembly of the electrical extraction system shown in FIG. 1. In FIG. 7, processor assembly 28 (FIG. 1) features a single processor unit 200 which includes processor unit housing 202, processor inlet unit 204, processor outlet unit 206, and two sets of three electrodes 208 and 210. By way of central control unit 34, the electrodes are connected and operate according to multiple phase electrical power generated by power supply unit 60. Either electrode set 208 or 210 is connected to a neutral, while the second electrode set 210 or 208, respectively, is connected to phase. In this processor assembly configuration, a liquid heat exchanger unit 212, a vapor condenser unit 214, and a non-condensing gas separator unit 216 are included as part of processor unit 200. This processor unit configuration is especially suitable in applications of electrical extraction for reducing undesirable levels of organic compounds from biological matter originating from municipal sewage and related sources of waste (see Example 7 below).

Referring again to extraction system 10 of FIG. 1, separator unit 220 receives processor effluent 50 exiting processor assembly 28 flowing through conduit 56 via separator inlet unit 222. Separator unit 220 mechanically separates processor effluent 50 into extract 224 and solids 226, where extract 224 include the target extract organic matter. Extract 224 and solids 226 exit separator 220 via separator liquids outlet unit 228 and separator solids outlet unit 230, respectively. Separator 220 is in electronic communication with central control unit 34 via control/data links 232.

Solids collection unit 234 receives solids 226 from conduit 236 via solids collection inlet unit 238. Collected solids 226 are either discarded or are further processed by another system such as a solids waste processing system. Solids collection unit 234 is in electronic communication with central control unit 34 via control/data links 240.

Extract filtration unit 242 receives extract 224 exiting separator 220 through conduit 242 via extract filtration inlet unit 246. Inside extract filtration unit 242, extract 224 is filtered, preferably through a filter medium such as a sieve having 120 micron size sieves. Extract filtration unit 242 removes undesirable particles and other relatively large sized impurities from extract 224, thereby forming a purer form of extract 224'. Extract 224' exits extract filtration unit 242 via extract filtration outlet unit 248 and flow through conduit 250 for final collection by extract collection unit 252. Extract filtration unit 242 is in electronic communication with central control unit 34 via control/data links 254.

Extract collection unit 252 receives extract 224' via extract collection inlet unit 256. Extracts so obtained are used as part of raw materials for manufacturing a diversity of end products. Extract collection unit is in electronic communication with central control unit 34 via control/data links 258.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Reference is now made to the following examples, which together with the above descriptions, illustrate the invention in a non-limiting fashion.

Examples of intracellular matter electrically extracted from corresponding biological matter used in the processor feed mixture by implementing the process and system for electrical extraction of the present invention include: Example 1: highly concentrated liquid fertilizer, including valuable elements and nutrients such as nitrogen, phosphorous, potassium, and their oxides, from solid animal compost; Examples 2–3: valuable substances, such as elements, nutrients, and organic compounds, from plant matter such as dried roots; Example 4: oils from plant matter such as citrus peels; Examples 5–6: fats and oils from animal solids such as fish or poultry solid waste from a fish or poultry processing facility; and, Example 7: inactivation of biological matter characterized by undesirable high levels of odor, COD, and BOD present in liquid organic sewage such as raw municipal sewage and related sources of waste.

Example 1

Highly Concentrated Liquid Fertilizer from Animal Solids

Processor feed featured animal solids, including partially composted poultry manure, and cow compost, mixed with water, with animal solids/water volume ratios in the range of 1/2 to 1/5. Processor assembly batch mode configurations of FIGS. 4A and 4B were used, where each processor unit was 20 liters in volume, surface area of each electrode was about 400 cm, and distance between outer and middle electrode was about 12 cm (FIG. 4A).

Electrical power included voltage of about 40–200 volts and current of about 20–40 amps. Processor mixture temperature was at about 95–100° C. Electrical extraction parameters were: (i) electrical current density of about 0.05–0.15 $A/m^2$, (ii) electric field strength of about 0.1 V/m, (iii) voltage time derivative of about $10^6$ V/s, (iv) pulse frequency of about 60 Hz, (v) pulse package duration of about 1 second, (vi) pause duration of about 1 second, (vii) pulse package/pause ratio of about 1/1, (viii) cycle time of about 2 seconds, and (ix) treatment time of about 30 minutes.

Chemical analysis was performed on the highly concentrated liquid fertilizer electrically extracted from the animal solids feed mixture, and the results are shown in Table 1.

TABLE 1

Profile of Highly Concentrated Liquid Fertilizer Electrically Extracted From Solid Animal Compost

| Chemical analysis (ppm) | | | Nutrients available for first crop (lbs/1,000 gallons) | | |
| --- | --- | --- | --- | --- | --- |
| N | P | K | N | $P_2O_5$ | $K_2O$ |
| 3,943 | 777 | 4,481 | 19.6 | 10.4 | 35.9 |
| 4,139 | 841 | 4,823 | 20.1 | 11.2 | 38.6 |

For comparison, applying a standard procedure involving heating and pressing the same animal compost, followed by liquid extraction, resulted in a chemical analysis (ppm) of N: 2,400, P: 474, and K: 2,600, with nutrients available for first crop (lbs./1000 gallons) of N: 13.2, $P_2O_5$: 5.5, and $K_2O$: 20.6.

Example 2

Valuable Substances from Plant Matter

Processor feed featured dry roots of Echinecea angustifolia mixed with water and alcohol, with water/alcohol volume ratios in the range of 10/1 to 1/10, dry roots/(water plus alcohol) volume ratio of about 1/1 to 1/10, and volume of mixture was 3.5 liters. Processor assembly batch mode configurations of FIGS. 4A and 4B were used, where each processor unit was 20 liters in volume, surface area of each electrode was about 400 cm, and distance between outer and middle electrodes was about 12 cm (FIG. 4A).

Electrical power included voltage of about 100 volts and current of about 20 amps. Processor mixture temperature was at about 100° C. Electrical extraction parameters were: (i) electrical current density of about 0.08 $A/m^2$, (ii) electric field strength of about 0.15 V/m, (iii) voltage time derivative of about $10^7$ V/s, (iv) pulse frequency of about 50 Hz, (v) pulse package duration of about 1 second, (vi) pause duration of about 2 seconds, (vii) pulse package/pause ratio of about 1/2, (viii) cycle time of about 3 seconds, and (ix) treatment time of about 17 minutes.

The results of Example 2 showed that a substantially smaller amount of alcohol is needed for high yield extraction of desirable substances from plant matter, compared to other methods of extraction of substances from plant matter.

Example 3

Valuable Substances from Plant Matter

Processor feed featured dry roots of Echinecea angustifolia mixed with water and alcohol, with water/alcohol volume ratios in the range of 10/1 to 1/10, dry roots/(water plus alcohol) volume ratio of about 1/1, and volume of mixture was 3.5 liters. Processor assembly batch mode configurations of FIGS. 4A and 4B were used, where each processor unit was 20 liters in volume, surface area of each electrode was about 400 $cm^2$, and distance between outer and middle electrodes was about 12 cm (FIG. 4A).

Electrical power included voltage of about 100 volts and current of about 5.5 amps. Processor mixture temperature was at about 75° C. Electrical extraction parameters were: (i) electrical current density of about 0.08 $A/m^2$, (ii) electric field strength of about 0.15 V/m, (iii) voltage time derivative of about $10^7$ V/s, (iv) pulse frequency of about 50 Hz, (v) pulse package duration of about 1 second, (vi) pause duration of about 2 seconds, (vii) pulse package/pause ratio of about 1/2, (viii) cycle time of about 3 seconds, and (ix) treatment time of about 10 minutes.

In addition to electrically extracting elements and nutrients from the plant matter, valuable organic compounds such as phenols were obtained. About 40 percent higher yield of phenolic compounds was obtained using the electrical extraction process of the present invention compared to a procedure involving cold pressing followed by standard liquid extraction, where the standard procedure requires using about 50 percent more alcohol. The results of this example show that a substantially smaller amount of alcohol is needed for high yield extraction of desirable substances from plant matter, compared to other methods of extraction of substances from plant matter.

Example 4

Oils from Plant Matter

Processor feed featured pulp of orange peels mixed with water, with pulp/water volume ratios in the range 1/1 to 1/10, and volume of mixture was 2 liters. Processor assembly batch mode configurations of FIGS. 4A and 4B were used, where each processor unit was 20 liters in volume, surface area of each electrode was about 400 $cm^2$, and distance between outer and middle electrodes was about 12 cm (FIG. 4A).

Electrical power included voltage of about 40–45 volts and current of about 3 amps. Processor mixture temperature was at about 25° C. Electrical extraction parameters were: (i) electrical current density of about 0.06 $A/m^2$, (ii) electric field strength of about 0.2 V/m, (iii) voltage time derivative of about $10^7$ V/s, (iv) pulse frequency of about 100 Hz, (v) pulse package duration of about 0.1 seconds, (vi) pause duration of about 0.1 second, (vii) pulse package/pause ratio of about 1/1, (viii) cycle time of about 0.2 second, and (ix) treatment time of about 1 minute.

The results of Example 4 showed a substantial increase in oil yield in the range of between about 20 to about 200 percent compared to cold pressing followed by standard extraction of oils from plant matter.

Example 5

Oils from Animal Solids from a Fish Processing Facility

Processor feed featured 1 kilogram of cod fish liver solids mixed with water, with fish solids/water volume ratios in the range 1/1 to 1/10. Processor assembly batch mode configuration with multiple processor outlet units of FIG. 6A was used.

Electrical power included voltage of about 220 volts and current of about 20 amps. Processor mixture temperature was at about 90–100° C. Electrical extraction parameters were: (i) electrical current density of about 0.15 A/m$^2$, (ii) electric field strength of about 0.2 V/m, (iii) voltage time derivative of about 10$^6$ V/s, (iv) pulse frequency of about 50 Hz, (v) pulse package duration of about 3 seconds, (vi) pause duration of about 1 second, (vii)-pulse package/pause ratio of 3/1, (viii) cycle time of about 4 seconds, and (ix) treatment time of about 5 minutes.

The cod fish liver solids were subjected to two procedures, in order to show the significant gain in yield of cod liver oil obtainable by including the electrical extraction process for extracting the available cod liver oil. The first procedure involved directly cold pressing the cod fish liver solids without being preceded by the above described electrical extraction process. The second procedure involved first subjecting the cod fish liver solids to the electrical extraction process, followed by standard cold pressing. For the 1 kg sample of cod fish liver solids, the first procedure yielded 480–510 g of cod liver oil, and the second procedure, including electrical extraction, yielded 590–630 g of cod liver oil, an increase of about 25 percent.

Example 6

Oils from Animal Solids from a Poultry Processing Facility

Processor feed featured poultry fats sludge flotation mixed with water, with sludge/water volume ratios in the range 1/1 to 1/10. Processor assembly batch mode configuration with multiple processor outlet units of FIG. 6A was used.

Electrical power included voltage of about 240 volts and current of about 10 amps. Processor mixture temperature was at about 80–100° C. Electrical extraction parameters were: (i) electrical current density of about 0.15 A/m$^2$, (ii) electric field strength of about 0.24 V/m, (iii) voltage time derivative of about 10$^6$ V/s, (iv) pulse frequency of about 60 Hz, (v) pulse package duration of about 1 second, (vi) pause duration of about 1 second, (vii) pulse package/pause ratio of about 1/1, (viii) cycle time of about 2 seconds, and (ix) treatment time of about 10 minutes.

The results of this example showed about 100% recovery of oils from the feed of poultry fats sludge. For example, electrically extracting poultry fats sludge yielded about 1900 mg fats per liter, compared to about 350 mg fats per liter by using a flotation method.

Example 7

Inactivation of Biological Matter Having Undesirable High Levels of Odor, COD, and BOD from Liquid Organic Sewage Processor feed featured 2 liters of liquid organic sewage, such as raw municipal sewage, including biological matter having undesirable high levels of odor, COD, and BOD mixed with water, with sewage/water volume ratios in the range 1/1 to 1/10. Processor assembly continuous mode configuration with a liquid heat exchanger of FIG. 7 was used.

Electrical power included voltage of about 100 volts and current of about 2.5 amps. Processor mixture temperature was at about 40° C. Electrical extraction parameters were: (i) electrical current density of about 0.15 A/m$^2$, (ii) electric field strength of about 0.1 V/m, (iii) voltage time derivative of about 10$^7$ V/s, (iv) pulse frequency of about 1000 Hz, (v) pulse package duration of about 1 second, (vi) pause duration of about 1 second, (vii) pulse package/pause ratio of about 1/1–1/10, (viii) cycle time of about 2 seconds, and (ix) treatment time of about 5 minutes.

The results of this example showed a dramatic decrease in COD from about 11000 to about 5000.

While the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A process for electrical extraction and recovery of intracellular matter from biological matter, the process comprising the steps of:

(a) supplying a mixture of the biological matter and an electro-conductive liquid to a processor assembly;

(b) electrifying said mixture by transmitting into said mixture at least one series of at least two cycles of electrical current having field strength less than 10$^3$ V/m and pulse frequency in a range of between about 50 Hz to about 100 Hz, each of said at least two cycles includes at least one pulse package of said electrical current having a pre-determined duration in a range of between about 1 second to about 10 seconds and at least one pause of said electrical current having a pre-determined duration in a range of between about 1 second to about 10 seconds, thereby releasing the intracellular matter from cells of the biological matter; and (c) recovering the released intracellular matter.

2. The process of claim 1, wherein each of said at least two cycles of said at least one pulse package and said at least one pause of said electrical current is characterized by at least one additional parameter selected from the group consisting of:

(i) density of said electrical current is in a range of between about 10$^2$ to about 10$^4$ A/m$^2$;

(ii) voltage time derivative of said electrical current is in a range of between about 10$^6$ to about 10$^8$ V/s;

(iii) ratio of said duration of said pulse package to said duration of said pause is in a range of between about 1/1 to about 1/10;

(iv) duration of each of said at least two cycles is in a range of between about 2 seconds to about 50 minutes; and (v) duration of said at least one series of said at least two cycles is in a range of between about 5 seconds to about 60 minutes.

3. The process of claim 1, whereby said electrical current is generated by a power supply unit and is controlled and modulated by a central control unit operating according to phase-pulse regulation, said phase-pulse regulation includes a neutral and at least three phases for regulating said electrical current.

4. The process of claim 1, whereby said pulse package of said electrical current is characterized by polarity selected from the group consisting of unipolar pulses and bipolar pulses, said unipolar pulses being a sequence of said pulses of identical shape and of same sign, said bipolar pulses being a sequence of said pulses of identical shape and of alternating sign, and said shape of said pulses is selected from the group consisting of triangular, rectangular, and sinusoidal.

5. The process of claim 1, wherein said releasing the intracellular matter from said cells of the biological matter takes place during each said pulse package of said electrical current and during each said pause of said electrical current.

6. The process of claim 1, wherein each of said at least two cycles of said at least one pulse package and said at least one pause of said electrical current is transmitted into said mixture by a mechanism positioned inside each of at least one processor unit, said at least one processor unit is positioned inside said processor assembly, said electrical current is generated by a power supply unit and said transmission of said electrical current is controlled and modulated by a central control unit in electronic communication with said processor assembly.

7. The process of claim 6, whereby said mechanism for electrifying the biological matter by transmitting into the biological matter said at least one series of said at least two cycles of said at least one pulse package and said at least one pause of said electrical current includes at least two electrodes, each of said at least two electrodes is positioned inside each of said at least one processor unit.

8. The process of claim 1, wherein said mixture enters, is electrified by said electrical current, and exits said processor assembly including at least one processor unit, whereby said processor assembly is configured and operates according to a mode selected from the group consisting of a batch mode and a continuous mode.

9. The process of claim 1, wherein a ratio of the biological matter to said electro-conductive liquid in said mixture is in a range of between about 1/1 to about 1/100 by volume.

10. The process of claim 1, wherein said electro-conductive liquid includes a liquid selected from the group consisting of water, alcohol, and glycerin.

11. The process of claim 1, wherein said recovering comprises the steps:

(a) separating said released intracellular matter from solids using a liquids/solids separator unit, thereby forming a liquid extract including said released intracellular matter;

(b) filtering said liquid extract using an extract filtration unit, thereby forming a purer form of said liquid extract; and (c) collecting said purer form of said liquid extract using a liquids collection unit.

12. The process of claim 11, wherein said liquid extract is filtered through a filter medium having a filter pore size less than 200 microns.

* * * * *